United States Patent
Arnaud et al.

(10) Patent No.: US 9,115,121 B2
(45) Date of Patent: Aug. 25, 2015

(54) 1,3,5-TRIAZINE-2-AMINE DERIVATIVES, PREPARATION THEREOF AND DIAGNOSTIC AND THERAPEUTIC USE THEREOF

(71) Applicant: SANOFI, Paris (FR)

(72) Inventors: Joelle Arnaud, Paris (FR); Martine Artiaga, Paris (FR); Francis Barth, Paris (FR); Laurent Hortala, Paris (FR); Serge Martinez, Paris (FR); Pascale Roux, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/364,418

(22) PCT Filed: Dec. 11, 2012

(86) PCT No.: PCT/EP2012/075119
§ 371 (c)(1),
(2) Date: Jun. 11, 2014

(87) PCT Pub. No.: WO2013/087643
PCT Pub. Date: Jun. 20, 2013

(65) Prior Publication Data
US 2014/0343061 A1    Nov. 20, 2014

(30) Foreign Application Priority Data

Dec. 12, 2011 (FR) ...................... 11 61458

(51) Int. Cl.
| | |
|---|---|
| *C07D 251/16* | (2006.01) |
| *A61K 31/53* | (2006.01) |
| *C07D 413/04* | (2006.01) |
| *C07D 401/04* | (2006.01) |
| *C07D 403/04* | (2006.01) |
| *C07D 405/04* | (2006.01) |
| *C07D 409/04* | (2006.01) |
| *C07D 251/42* | (2006.01) |

(52) U.S. Cl.
CPC ............ *C07D 413/04* (2013.01); *C07D 251/16* (2013.01); *C07D 251/42* (2013.01); *C07D 401/04* (2013.01); *C07D 403/04* (2013.01); *C07D 405/04* (2013.01); *C07D 409/04* (2013.01); *C07B 2200/05* (2013.01)

(58) Field of Classification Search
CPC .. C07D 251/16; C07D 401/04; C07D 403/04; C07D 405/04; C07D 409/04; C07D 413/04; A61K 31/53; C07B 200/05
USPC .................. 544/211, 212; 514/245
See application file for complete search history.

(56) References Cited

U.S. PATENT DOCUMENTS

| | | | |
|---|---|---|---|
| 4,581,354 A | 4/1986 | Bell | |
| 5,532,237 A | 7/1996 | Gallant | |

FOREIGN PATENT DOCUMENTS

| | | |
|---|---|---|
| EP | 0833818 B1 | 4/1998 |
| WO | 0147897 A1 | 7/2001 |
| WO | 0147921 A1 | 7/2001 |
| WO | 0242269 A1 | 5/2002 |
| WO | 03097597 A2 | 11/2003 |
| WO | 2006044732 A2 | 4/2006 |
| WO | 2006069196 A1 | 6/2006 |
| WO | 2007057571 A1 | 5/2007 |
| WO | 2007064931 A2 | 6/2007 |
| WO | 2009091388 A2 | 7/2009 |

OTHER PUBLICATIONS

Miller et al. Pharmacol Rev 63:461-470, 2011.*
Cecil Textbook of Medicine, edited by Bennet, J.C., and Plum F., 20th edition, vol. 1, 1004-101 O, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Turner et al., Current Pharmaceutical Design. 2, 209-224, 1996.*
Sugar et al., Diagno Microbiol. Infect. Dis. 21" 129-133, 1995.*
Snyder et al., J. Med. Liban 48(4): 208-214, 2000. PubMed Abstract.*
Pimlott SL., Nucl. Med. Commun. 26(3): 183-188, 2005 (PubMed Abstract provided).*

(Continued)

*Primary Examiner* — Venkataraman Balasubramanian
(74) *Attorney, Agent, or Firm* — McDonnell Boehnen Hulbert & Berghoff LLP

(57) ABSTRACT

The present invention relates to compounds corresponding to formula (I) in which: —$R_1$ represents a substituted phenyl; —$R_2$ represents: —a substituted phenyl; —a heteroaromatic group, the said group being unsubstituted or substituted one or more times; —$R_3$ represents a group Alk; —$R_4$ represents a hydrogen atom or a ($C_1$-$C_4$)alkyl; —$R_5$ represents a hydrogen atom, a ($C_3$-$C_6$)cycloalkyl or a ($C_1$-$C_4$)alkyl-O-Alk; —or alternatively $R_4$ and $R_5$, together with the nitrogen atom to which they are attached, constitute a heterocyclic radical chosen from: azetidin-1-yl, pyrrolidin-1-yl, piperid-1-yl, morpholin-4-yl; —$R_6$ represents a group —COOAlk, a group —$CONH_2$ or a group —$NHSO_2Alk$; —Alk represents a ($C_1$-$C_4$)alkyl, which is unsubstituted or substituted one or more times with a halogen atom; in the form of the base or of an acid-addition salt. Preparation process and diagnostic and therapeutic use.

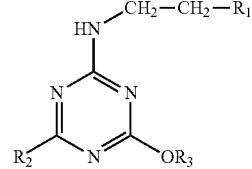

(I)

7 Claims, No Drawings

(56) References Cited

OTHER PUBLICATIONS

Benito, Cristina et al., "Neuroinflammation and the Glial Endocannabinoid System, Cannabinoids and the Brain," Springer 2008, 331-359.

Bois, Frederic et al., "Synthesis, radiolabeling and baboon SPECT imaging of 2β-carbomethoxy-3β-(3'-[123I]iodophenyl)tropane ([123I]YP256) as a serotonin transporter radiotracer," Science Direct, Nuclear Medicine and Biology 35, 2008, 53-59.

Bouaboula, Monsif et al., "Cell Biology and Metabolish: A Selective Inverse Agonist for Central a Selective Inverse Agonist for Central Mitogen-activated Protein Kinase Activation Stimulated by Insulin or Insulin-like Growth Factor 1: Evidence for a New Model of Receptor/Ligand Interactions," The Journal of Biological Chemistry, 1997, 272: 22330-22339.

Cota, D. et al., "Endogenous cannabinoid system as a modulator of food intake1," International Journal of Obesity (2003) 27, 289-301 Nature Publishing Group.

Evens, Nele, et al., "Synthesis, in vitro and in vivo evaluation of fluorine-18 labelled FE-GW405833 as a PET tracer for type 2 cannabinoid receptor imaging," Bioorganic & Medicinal Chemistry, 19, 2011 4499-4505.

Fernandes-Ruiz, Javier et al., "Cannabinoid CB2 receptor: a new target for controlling neural cell survival?," Trends in Pharmacological Sciences, vol. 28 No. 1, 2006, 40-45.

Fujinaga, Masayuki et al., "Radiosynthesis of novel carbon-11-labeled triaryl ligands for cannabinoid-type 2 receptor,"Bioorganic & Medicinal Chemistry Letters, 20, 2010, 1565-1568.

Garcia, "21st Annual Symposium of the International Cannabinoid Research Society," Pheasant Run, St. Charles, Il, Jul. 5-10, 2011.

Horti, Andrew G et al., "Synthesis and biodistribution of [11C]A-836339, a new potential radioligand for PET imaging of cannabinoid type 2 receptors (CB2)," Bioorganic & Medicinal Chemistry 18, 2010, 5202-5207.

Howlett, A. C., "International Union of Pharmacology. XXVII. Classification of Cannabinoid Receptors," Pharmacological Reviews, vol. 54, No. 2, 2002,161-202.

Klein, Thomas, et al., "Cannabinoid receptors and immunity," Immunology Today, vol. 19, No. 8, Aug. 1998, 373-381.

Lefoix, Myriam et al., "Versatile and Convenient Methods for the Synthesis of C-2 and C-3 Functionalised 5-Azaindoles," Synthesis 2005, No. 20, 3581-3588.

Matsuda, Lisa et al., "Structure of a cannabinoid receptor and functional expression of the cloned cDNA," Letters to Nature, vol. 346, Aug. 1990, 561-564.

Mizuta, Masahiro et al., "Fluorescent Pyrimidopyrimidoindole Nucleosides: Control of Photophysical Characterizations by Substituent Effects," JOC Article, J. Org, Chem. 2007, 72, 5046-5055.

Miller, Philip et al., "Synthesis of 11C, 18F, 15O, and 13N Radiolabels for Positron Emission Tomography," Angew. Chem. Int Ed. 2008, 47, 8998-9033.

Munro, Sean et al., "Molecular characterization of a peripheral receptor for cannabinoids," Nature, vol. 365, Sep. 1993, 61-65.

Paton, W.D.M, "Pharmacology of Marijuana," Annu. Rev. Pharmacol. 1975, 15:191-220.

Pertwee, Roger G., "Cannabinoid receptors and pain," Progress in Neurobiology, 63, 2001, 569-611.

Portier, Marielle, "SR 144528, an Antagonist for the Peripheral Cannabinoid Receptor that Behaves as an Inverse Agonist," The Journal of Pharmacology and Experimental Therapeutics, vol. 288, No. 2, Mar. 1998, 582-589.

Rinaldi-Carmona, Murielle, et al. "Characterization of Two Cloned Human CB1 Cannabinoid Receptor Isoforms," The Journal of Pharmacology and Experimental Therapeutics, vol. 278, No. 2, Nov. 1995, 871-878.

Rinaldi-Carmona, Murielle, et al. "SR 144528, the First Potent and Selective Antagonist of the CB2 Cannabinoid Receptor," The Journal of Pharmacology and Experimental Therapeutics, vol. 284, No. 2, Oct. 1997, 644-650.

Vasquez, Enrique et al., "A Non-cryogenic Method for the Preparation of 2-(Indolyl) Borates, Silanes, and Silanols," J. Org. Chem. 2002, 67, 7551-7552.

Zhang, Ming-Rong et al, Synthesis and evaluation of N-(5-fluoro-2-phenoxyphenyl)-N-(2-[18F]fluoromethoxy-d2-5-methoxybenzyl)acetamide: a deuteriumsubstituted radioligand for peripheral benzodiazepine receptor, Science Direct, Bioorganic & MedicinalChemistry 13, 2005, 1811-1818.

Ganesh A. Thakur, Ritesh Tichkule, Shama Bajaj and Alexandros Makriyannis, "Latest Advances in Cannabinoid Receptor Agonists" Expert Opn. Ther. Pat. (2009) 19(12).

French Search Report for French Patent Application No. FR1161458 dated Mar. 23, 2012.

International Search Report for International Patent Application No. PCT/EP2012/075119 dated Jan. 28, 2013 (mailed Feb. 5, 2013).

* cited by examiner

1,3,5-TRIAZINE-2-AMINE DERIVATIVES, PREPARATION THEREOF AND DIAGNOSTIC AND THERAPEUTIC USE THEREOF

This application is a national stage application under 35 U.S.C. §371 of International Application No. PCT/EP2012/075119, filed Dec. 11, 2012, the disclosure of which is explicitly incorporated by reference herein.

The present invention relates to novel 1,3,5-triazine-2-amine derivatives with affinity for the type-2 cannabinoid ($CB_2$) receptors, to the preparation thereof and to the diagnostic and therapeutic use thereof.

$\Delta^9$-THC is the main active constituent extracted from *Cannabis sativa* [Paton, Annual Review in Pharmacology (1975) 15: 191-220].

Numerous articles have described not only psychotropic effects of cannabinoids, but also their influence on the immune function [Klein et al, Immunology Today (1998) 19: 373-381], pain control [Pertwee, Progress in Neurobiology (2001) 63: 569-611], food intake [Cota et al. International Journal of Obesity (2003) 27: 289-301] and numerous other biological functions [Nahas et al. Marihuana and medicine (1999) Humana Press: Totowa, N.J., USA].

The effects of cannabinoids are due to an interaction with high-affinity specific receptors, coupled to the G proteins, present at the central and peripheral level [Howlett et al., Pharmacological Reviews (2002) 54: 161-2002].

The central effects of cannabinoids arise from a first type of receptor ($CB_1$) present mainly in the brain, but also peripherally [Matsuda et al., Nature (1990) 346: 561-564]. Moreover, Munro et al. [Nature (1993) 365: 61-65] have cloned a second type of cannabinoid receptor known as $CB_2$, which is present peripherally and in particular in cells of the immune system [Howlett et al., Pharmacological Reviews (2002) 54: 161-202]. Recent studies have also demonstrated weak expression of the $CB_2$ receptor in certain structures of the central nervous system, in particular in the glial cells (microglial cells and astrocytes), but above all substantial overexpression of these glial receptors under pathological conditions involving neuroinflammation, such as Alzheimer's disease, Huntington's chorea, amyotrophic lateral sclerosis, multiple sclerosis, HIV-related encephalopathy, Down's syndrome and ischaemia [Fernandez-Ruiz et al., Trends Pharmacol. Sci. (2007) 28, 39-45, and Benito et al. Cannabinoids and the Brain, Springer Ed. (2008), 331-359], and also in Parkinson's disease [Garcia et al. ICRS (2011) P3-2].

Certain indole derivatives have been cited in the prior art as having the affinity for the $CB_2$ receptors: mention may be made of patent applications U.S. Pat. No. 5,532,237, EP 833 818, U.S. Pat. No. 4,581,354, WO 2002/42269, WO2003/097597, WO 2006/069 196 and WO 2007/057 571.

International patent application WO 2001/047 921 describes triazine derivatives as kinase inhibitors. International patent application WO 2009/091 388 describes triazine derivatives with antiviral activity.

Moreover, the use of $CB_2$ ligands radiolabelled with carbon-11 or fluorine-18 as PET (positron emission tomography) markers has been described by several authors [A M. Fujinaga et al. Bioorg. Med. Chem. Lett. (2010) 20, 1565-1568; A. G. Horti et al. Bioorg. Med. Chem. (2010) 18, 5202-5207; N. Evens et al. Bioorg. Med. Chem. (2011) 19, 4499-4505].

Novel 1,3,5-triazine-2-amine derivatives that have high affinity and great selectivity towards the cannabinoid $CB_2$ receptors have now been found. These compounds have a modulatory effect on the activity of the $CB_2$ receptors. The term "modulatory effect" especially means agonist, antagonist and/or inverse agonist effects.

A subject of the present invention is compounds corresponding to formula (I):

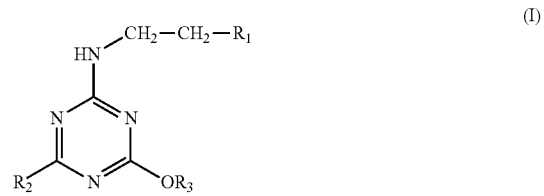

in which:
R$_1$ represents a phenyl substituted one or more times with substituents independently chosen from a halogen atom, a group -Alk and a group —OAlk;

R$_2$ represents:
a phenyl substituted one or more times with substituents independently chosen from a halogen atom, a cyano, a hydroxyl, a nitro, a group -Alk, —OAlk, —SAlk, —SO$_2$Alk, —COAlk, —SO$_2$NR$_4$R$_5$, a —(C$_1$-C$_6$)alkyl-OH, a —(C$_1$-C$_4$)alkyl-COOAlk, a —O—(C$_1$-C$_4$)alkyl-R$_6$, a methylenedioxy and an ethylenedioxy;
a heteroaromatic group, the said group being unsubstituted or substituted one or more times with substituents independently chosen from a halogen atom, a cyano, a group -Alk, a group —OAlk, a group —SAlk or —N(Alk)$_2$;

R$_3$ represents a group Alk;
R$_4$ represents a hydrogen atom or a (C$_1$-C$_4$)alkyl;
R$_5$ represents a hydrogen atom, a (C$_3$-C$_6$)cycloalkyl or a (C$_1$-C$_4$)alkyl-O-Alk;
or alternatively R$_4$ and R$_5$, together with the nitrogen atom to which they are attached, constitute a heterocyclic radical chosen from: azetidin-1-yl, pyrrolidin-1-yl, piperid-1-yl, morpholin-4-yl;
R$_6$ represents a group —COOAlk, a group —CONH$_2$ or a group —NHSO$_2$Alk;
Alk represents a (C$_1$-C$_4$)alkyl, which is unsubstituted or substituted one or more times with a halogen atom.

The compounds of formula (I) may contain one or more radioisotopes enabling their detection via diagnostic methods such as, for example, PET (positron emission tomography) imaging or SPET (single-photon emission tomography, also known as SPECT) imaging. In particular, the carbon, fluorine or iodine atoms may be replaced with carbon-11, fluorine-18 or iodine-123 isotopes when they are contained, respectively, in a methoxy group, a fluoroalkyl group such as —CH$_2$F or an iodoalkyl group such as —CH$_2$I or iodoaryl. The compounds of formula (I) may also contain one or more deuterium atoms. The compounds thus radiolabelled form part of the invention.

The compounds of formula (I) may comprise one or more asymmetric carbon atoms. They may therefore exist in the form of enantiomers or diastereoisomers. These enantiomers, diastereoisomers, and also mixtures thereof, including racemic mixtures, form part of the invention.

The compounds of formula (I) may exist in the form of bases or addition salts with acids. Such addition salts form part of the invention.

These salts are advantageously prepared with pharmaceutically acceptable acids, but salts of other acids that are of use, for example, for purifying or isolating the compounds of formula (I) also form part of the invention.

The term $(C_1-C_4)$ alkyl or, respectively, $(C_1-C_6)$ alkyl means a linear or branched carbon radical of 1 to 4 carbon atoms or, respectively, of 1 to 6 carbon atoms, in particular such as: methyl, ethyl, propyl, isopropyl, butyl, isobutyl, tert-butyl, pentyl, hexyl.

The term $(C_1-C_4)$alkoxy means an oxygen atom linked to a linear or branched carbon radical of 1 to 4 carbon atoms such as a methoxy, ethoxy, propoxy, isopropoxy, butoxy, sec-butoxy or tert-butoxy radical.

The term $(C_3-C_6)$cycloalkyl means a cyclopropyl, cyclobutyl, cyclopentyl or cyclohexyl carbon radical.

The term halogen atom means a fluorine, chlorine, bromine or iodine atom.

The term heteroaromatic group means, for example, a pyridyl, thiadiazolyl, indolyl, indazolyl, imidazolyl, benzimidazolyl, benzotriazolyl, benzofuryl, benzothienyl, benzothiazolyl, benzisothiazolyl, quinolyl, isoquinolyl, benzoxazolyl, benzisoxazolyl, benzoxadiazolyl, isoxazolyl, benzopyranyl, thiazolyl, thienyl, furyl, chromenyl, isobenzofuryl, pyrrolyl, pyrazolyl, pyrazinyl, pyrimidinyl, pyridazinyl, indolizinyl, phthalazinyl, quinazolinyl, isothiazolyl, isochromanyl, chromanyl or 1H-pyrrolo[2,3-b]pyridyl.

According to the present invention, preference is given to the compounds of formula (I) in which:

$R_1$ represents a phenyl substituted with a halogen atom or a group OAlk;

$R_2$ represents:
a phenyl substituted once or twice with substituents chosen independently from a halogen atom, a cyano, a hydroxyl, a nitro, a $(C_1-C_4)$alkyl, a $(C_1-C_4)$alkoxy, an —S—$(C_1-C_4)$alkyl, an —SO$_2$—$(C_1-C_4)$alkyl, a —CO—$(C_1-C_4)$alkyl, an —SO$_2$NR$_4$R$_5$, a $(C_1-C_6)$ alkyl-OH, a $(C_1-C_4)$alkyl-COO—$(C_1-C_4)$alkyl, an —O—$(C_1-C_4)$alkyl-R$_6$, a methylenedioxy and an ethylenedioxy;
a heteroaromatic group chosen from a pyridyl, an indolyl, a benzofuryl, a benzothienyl, a benzoxadiazolyl, a quinolyl and an isoquinolyl; the said group being unsubstituted or substituted once or twice with a halogen atom, a cyano, a $(C_1-C_4)$alkyl, a $(C_1-C_4)$ alkoxy, an —S—$(C_1-C_4)$alkyl or an N—[$(C_1-C_4)$ alkyl]$_2$;

$R_3$ represents a group Alk;

$R_4$ represents a hydrogen atom;

$R_5$ represents a hydrogen atom, a $(C_3-C_6)$cycloalkyl or a $(C_1-C_4)$alkyl-O-Alk;

or alternatively $R_4$ and $R_5$, together with the nitrogen atom to which they are attached, constitute a morpholin-4-yl radical;

$R_6$ represents a group —COO—$(C_1-C_4)$alkyl, a group —CONH$_2$ or a group —NHSO$_2$—$(C_1-C_4)$alkyl;

Alk represents a $(C_4-C_4)$alkyl, which is unsubstituted or substituted one or more times with a halogen atom; in the form of the base or of an acid-addition salt.

Preference is particularly given to the compounds of formula (I) in which:

$R_1$ represents a 4-fluorophenyl, a 4-(fluoromethoxy)phenyl, a 4-(difluoromethoxy)phenyl or a 4-(trifluoromethoxy)phenyl;

$R_2$ represents:
a 3-methoxyphenyl, a 3-isopropoxyphenyl, a 3,4-dimethoxyphenyl, a 3-nitrophenyl, a 4-(methylthio) phenyl, a 3-(3-methoxy-3-oxopropyl)phenyl, a 3,4-methylenedioxyphenyl, a 3,4-ethylenedioxyphenyl, a 3-(methylsulfonyl)phenyl, a 3-acetyl-2-fluorophenyl, a 3-[(cyclopropylamino)sulfonyl]phenyl, a 3-[(cyclopropylamino)sulfonyl]-4-methoxyphenyl, a 4-chloro-3-(1-hydroxy-1-methylethyl)phenyl, a 4-fluoro-3-(1-hydroxy-1-methylethyl)phenyl, a 4-(1-hydroxy-1-methylethyl)-3-methoxyphenyl, a 3-(1-hydroxy-1-methylethyl)phenyl, a 3-(1-hydroxy-1-methylethyl)-4-methoxyphenyl, a 3-[(cyclopropylamino)sulfonyl]-4-(hydroxymethyl) phenyl, a 4-chloro-3-{[(2-methoxyethyl)amino] sulfonyl}phenyl, a 4-chloro-3-morpholin-4-ylsulfonyl)phenyl, a 3-[(cyclopropylamino)sulfonyl]-4-methylphenyl, a 3-(1-ethyl-1-hydroxypropyl)phenyl, a 4-chloro-3-hydroxyphenyl, a 4-chloro-3-[(cyclopropylamino)sulfonyl]phenyl, a 4-chloro-3-(2-ethoxy-2-oxoethoxy)phenyl, a 3-cyano-4-methoxyphenyl, a 3-(2-amino-2-oxoethoxy)-4-chlorophenyl, a 4-chloro-3-{3-[(methylsulfonyl) amino]propoxy}phenyl;
a 6-(dimethylamino)pyridin-3-yl, a 5-bromo-1H-indol-2-yl, a 4-chloro-1H-indol -2-yl, a 5-chloro-1H-indol-2-yl, a 5-fluoro-1H-indol-2-yl, a 6-fluoro-1H-indol-2-yl, a 5-methyl-1H-indol-2-yl, a 4-methoxy-1H-indol-2-yl, a 5-methoxy-1H -indol-2-yl, a 5-cyano-1H-indol-2-yl, a 5-(methylthio)-1H-indol-2-yl, a 1H-indol -4-yl, a 1H-indol-5-yl, a 1H-indol-6-yl, a 1-benzofuran-2-yl, a 2,1,3-benzoxadiazol-5-yl, a quinolin-3-yl, a quinolin-4-yl, a quinolin-5-yl, a quinolin -6-yl, a quinolin-8-yl, a 5-fluoroquinolin-8-yl, an 8-methylquinolin-5-yl, an 8-methoxy-2-methylquinolin-5-yl, an isoquinolin-4-yl, an isoquinolin-5-yl, a 1-benzothien-2-yl, a 5-methoxy-1-benzofuran-2-yl, a 5-chloro-1-benzofuran-2-yl;

$R_3$ represents a methyl or a fluoromethoxy;
in the form of the base or of an acid-addition salt.

Among the compounds of formula (I) that are subjects of the invention mention may be made especially of the following compounds:

N-[2-(4-fluorophenyl)ethyl]-4-methoxy-6-(3-methoxyphenyl)-1,3,5-triazin-2-amine;

(4-chloro-1H-indol-2-yl)-N-[2-(4-fluorophenyl)ethyl]-6-methoxy-1,3,5-triazin-2-amine;

4-(3,4-dimethoxyphenyl)-N-[2-(4-fluorophenyl)ethyl]-6-methoxy-1,3,5-triazin-2-amine;

4-(5-fluoro-1H-indol-2-yl)-N-[2-(4-fluorophenyl)ethyl]-6-methoxy-1,3,5-triazin -2-amine;

4-(4-chloro-1H-indol-2-yl)-N-{2-[4-(difluoromethoxy)phenyl]ethyl}-6-methoxy -1,3,5-triazin-2-amine;

4-(5-bromo-1H-indol-2-yl)-N-[2-(4-fluorophenyl)ethyl]-6-methoxy-1,3,5-triazin -2-amine;

4-(5-chloro-1H-indol-2-yl)-N-[2-(4-fluorophenyl)ethyl]-6-methoxy-1,3,5-triazin -2-amine;

2-(4-{[2-(4-fluorophenyl)ethyl]amino}-6-methoxy-1,3,5-triazin-2-yl)-1H-indole -5-carbonitrile;

N-[2-(4-fluorophenyl)ethyl]-4-methoxy-6-(5-methyl-1H-indol-2-yl)-1,3,5-triazin -2-amine;

N-[2-(4-fluorophenyl)ethyl]-4-(5-fluoroquinolin-8-yl)-6-methoxy-1,3,5-triazin-2-amine;

2-[2-chloro-5-(4-{[2-(4-fluorophenyl)ethyl]amino}-6-methoxy-1,3,5-triazin-2-yl)phenyl]propan-2-ol;

N-cyclopropyl-3-(4-{[2-(4-fluorophenyl)ethyl]amino}-6-methoxy-1,3,5-triazin-2-yl)benzenesulfonamide;

2-[4-(4-{[2-(4-fluorophenyl)ethyl]amino}-6-methoxy-1,3, 5-triazin-2-yl)-2-methoxyphenyl]propan-2-ol;

2-{2-chloro-5-[4-({2-[4-(difluoromethoxy)phenyl] ethyl}amino)-6-methoxy-1,3,5-triazin-2-yl] phenyl}propan-2-ol;

2-{2-chloro-5-[4-methoxy-6-({2-[4-(trifluoromethoxy)phenyl]ethyl}amino)-1,3,5-triazin-2-yl]phenyl}propan-2-ol;

4-(1-benzothien-2-yl)-N-[2-(4-fluorophenyl)ethyl]-6-methoxy-1,3,5-triazin-2-amine;
N-[2-(4-fluorophenyl)ethyl]-4-methoxy-6-(5-methoxy-1-benzofuran-2-yl)-1,3,5-triazin-2-amine;
2-{5-[4-({2-[4-(difluoromethoxy)phenyl]ethyl}amino)-6-methoxy-1,3,5-triazin-2-yl]-2-methoxyphenyl}propan-2-ol;
4-(5-chloro-1-benzofuran-2-yl)-N-[2-(4-fluorophenyl)ethyl]-6-methoxy-1,3,5-triazin-2-amine;
2-chloro-5-(4-{[2-(4-fluorophenyl)ethyl]amino}-6-methoxy-1,3,5-triazin-2-yl)-N-(2-methoxyethyl)benzenesulfonamide;
4-[4-chloro-3-(morpholin-4-ylsulfonyl)phenyl]-N-[2-(4-fluorophenyl)ethyl]-6-methoxy-1,3,5-triazin-2-amine;
2-{2-methoxy-5-[4-methoxy-6-({2-[4-(trifluoromethoxy)phenyl]ethyl}amino)-1,3,5-triazin-2-yl]phenyl}propan-2-ol;
N-cyclopropyl-5-[4-({2-[4-(difluoromethoxy)phenyl]ethyl}amino)-6-methoxy -1,3,5-triazin-2-yl]-2-methylbenzenesulfonamide;
2-[3-(4-{[2-(4-fluorophenyl)ethyl]amino}-6-methoxy-1,3,5-triazin-2-yl)phenyl]propan-2-ol;
3-[3-(4-{[2-(4-fluorophenyl)ethyl]amino}-6-methoxy-1,3,5-triazin-2-yl)phenyl]pentan-3-ol;
2-[5-(4-{[2-(4-fluorophenyl)ethyl]amino}-6-methoxy-1,3,5-triazin-2-yl)-2-methoxyphenyl]propan-2-ol;
N-cyclopropyl-5-(4-{[2-(4-fluorophenyl)ethyl]amino}-6-methoxy-1,3,5-triazin-2-yl)-2-(hydroxymethyl)benzenesulfonamide;
N-cyclopropyl-3-[4-({2-[4-(difluoromethoxy)phenyl]ethyl}amino)-6-methoxy -1,3,5-triazin-2-yl]benzenesulfonamide;
2-chloro-5-(4-{[2-(4-fluorophenyl)ethyl]amino}-6-methoxy-1,3,5-triazin-2-yl)phenol;
2-chloro-N-cyclopropyl-5-(4-{[2-(4-fluorophenyl)ethyl]amino}-6-methoxy-1,3,5-triazin-2-yl)benzenesulfonamide;
ethyl [2-chloro-5-(4-{[2-(4-fluorophenyl)ethyl]amino}-6-methoxy-1,3,5-triazin-2-yl)phenoxy]acetate;
5-(4-{[2-(4-fluorophenyl)ethyl]amino}-6-methoxy-1,3,5-triazin-2-yl)-2-methoxybenzonitrile;
2-[2-chloro-5-(4-{[2-(4-fluorophenyl)ethyl]amino}-6-methoxy-1,3,5-triazin-2-yl)phenoxy]acetamide;
N-{3-[2-chloro-5-(4-{[2-(4-fluorophenyl)ethyl]amino}-6-methoxy-1,3,5-triazin-2-yl)phenoxy]propyl}methanesulfonamide;
N-(3-{2-chloro-5-[4-({2-[4-(difluoromethoxy)phenyl]ethyl}amino)-6-methoxy -1,3,5-triazin-2-yl]phenoxy}propyl)methanesulfonamide;
2-{2-chloro-5-[4-({2-[4-(difluoromethoxy)phenyl]ethyl}amino)-6-methoxy-1,3,5-triazin-2-yl]phenoxy}acetamide;
2-{2-chloro-5-[4-({2-[4-(fluoromethoxy)phenyl]ethyl}amino)-6-methoxy-1,3,5-triazin-2-yl]phenyl}propan-2-ol;
2-{5-[4-({2-[4-(fluoromethoxy)phenyl]ethyl}amino)-6-methoxy-1,3,5-triazin-2-yl]-2-methoxyphenyl}propan-2-ol;
2-{2-chloro-5-[4-(fluoromethoxy)-6-{[2-(4-fluorophenyl)ethyl]amino}-1,3,5-triazin-2-yl]phenyl}propan-2-ol;
2-{5-[4-(fluoromethoxy)-6-{[2-(4-fluorophenyl)ethyl]amino}-1,3,5-triazin-2-yl]-2-methoxyphenyl}propan-2-ol;
in the form of the base or of an acid-addition salt.

In the text hereinbelow, the term "protecting group PG" means a group that can be, firstly, protect a reactive function such as a hydroxyl or an amine during the synthesis and, secondly, regenerate the intact reactive function at the end of the synthesis. Examples of protecting groups and also of protection and deprotection methods are given in *Protective Group in Organic Synthesis*, Greene et al., 4th Edition (John Wiley & Sons, Inc., New York), 2007.

In the text hereinbelow, the term "leaving group" means a group that can be readily cleaved from a molecule by breaking a heterolytic bond, with loss of an electron pair. This group may thus be readily replaced with another group, for example during a substitution reaction. Such leaving groups are, for example, halogens or an activated hydroxyl group such as a methanesulfonate, benzenesulfonate, p-toluenesulfonate, triflate, acetate, etc. Examples of leaving groups and also references for their preparation are given in *Advanced Organic Chemistry*, M. B. Smith and J. March, 6th Edition, Wiley Interscience, 2007, pp. 496-501.

In accordance with the invention, the compounds of formula (I) may be prepared according to a process that is characterized in that:

a compound of formula:

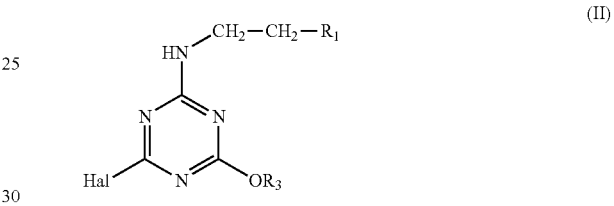

in which $R_1$ and $R_3$ are as defined for a compound of formula (I) and, Hal represents a halogen atom, is reacted with a boronic acid or an ester derivative of this acid of formula:

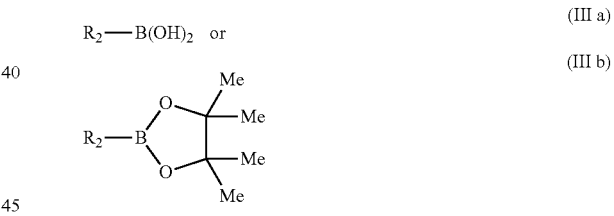

in which $R_2$ is as defined for a compound of formula (I).

Optionally, the compound of formula (I) is converted into a salt thereof with mineral or organic acids.

The reaction is performed in the presence of a palladium complex, for instance tetrakis(triphenylphosphine)palladium or 1,1'-bis(diphenylphosphino)ferrocenepalladium(II) dichloride, and in the presence of a base, for instance caesium carbonate or sodium carbonate. The solvent used is, for example, 1,2-dimethoxyethane, toluene, acetonitrile, methanol, ethanol or water, or a mixture of these solvents. The reaction temperature is between room temperature and the reflux point of the solvent.

Compounds of formula (I) may also be prepared from other compounds of formula (I) as a function of the nature of the substituents.

Thus, for example, a compound of formula (I) in which $R_2$ represents a phenyl substituted with a group —O—$(C_1$-$C_4)$alkyl-$R_6$ in which $R_6$=COOAlk may be prepared by reacting a compound of formula (I) in which $R_2$ represents a phenyl substituted with a hydroxyl with a compound of formula Hal-$(C_1$-$C_4)$alkyl-COOAlk. The reaction takes place in the presence of a base such as potassium carbonate, in a solvent such as acetone and at a temperature of between 0° C. and the reflux temperature of the solvent.

Similarly, a compound of formula (I) in which $R_2$ represents a phenyl substituted with a group —O—$(C_1$-$C_4)$alkyl-$R_6$ in which $R_6$=—$CONH_2$ may be prepared by acid or base hydrolysis of a corresponding compound of formula (I) in which $R_6$=—COOAlk, followed by reaction of the intermediate acid obtained with aqueous ammonia, in the presence of a coupling agent such as 1,1'-carbonyldiimidazole.

A compound of formula (I) in which $R_3$ represents a $(C_1$-$C_4)$alkyl substituted with one or more halogen atoms may also be prepared by reacting a compound of formula (I) in which $R_3$=$CH_3$ with sodium methoxide, followed by reacting the intermediate hydroxyl compound obtained with a $(C_1$-$C_4)$ alkyl halide substituted with one or more halogen atoms, in the presence of a strong base such as sodium hydride or with a corresponding sulfonate derivative, in the presence of a base such as caesium carbonate.

According to one variant of the process, compounds of formula (I) may be prepared from corresponding intermediate compounds.

Thus, for example, compounds of formula (I) in which $R_1$ represents a phenyl substituted with a group OAlk in which Alk=$(C_1$-$C_4)$alkyl substituted with one or more halogen atoms may be prepared by reacting the corresponding phenolic compound with a $(C_1$-$C_4)$alkyl sulfonate substituted with one or more halogen atoms, in the presence of a base such as caesium carbonate.

The compounds of formula (I) thus obtained may be subsequently separated from the reaction medium and purified according to standard methods, for example by crystallization or chromatography.

The compounds of formula (I) thus obtained are isolated in the form of the free base or of a salt, according to the standard techniques.

The compounds of formula (II) are prepared by reacting a compound of formula:

(IV)

Hal—[triazine with Hal, N, N, N, OR$_3$]

in which $R_3$ is as defined for a compound of formula (I) and Hal represents a halogen atom, preferably chlorine, with a compound of formula:

$H_2N$—$CH_2$—$CH_2$—$R_1$ (V)

in which $R_1$ is as defined for a compound of formula (I).

The reaction takes place in the presence of a base, for instance N,N-diisopropylethylamine, in a solvent such as acetonitrile and at a temperature of between 0° C. and room temperature.

The compounds of formulae (IIIa) and (IIIb) are commercial, known or prepared according to known methods such as those described in J. Org. Chem., 2002, 67, 7551-7552; J. Org. Chem., 2007, 72, 5046-5055; Synthesis, 2005, 20, 3581-3588; WO 2007/064 931.

The compounds of formula (IV) are commercial, known or prepared according to known methods. Thus, 2,4-dichloro-6-methoxy-1,3,5-triazine is commercial.

The compounds of formula (V) are commercial, known or prepared according to known methods such as those described in WO 2006/044 732.

In particular, the compounds of formula (V) may also be prepared according to Scheme I below in which $R_1$ is as defined for a compound of formula (I) and Alk represents a $(C_1$-$C_2)$alkyl.

SCHEME I $R_1$—$CH_2$—COOAlk $\xrightarrow{a_1}$ $R_1$—$CH_2$—$CH_2$—OH
(VI) (VII)

$\downarrow b_1$ $R_1$—$CH_2$—$CH_2$—$NH_2$ $\xleftarrow{c_1}$ $R_1$—$CH_2$—$CH_2$—N[phthalimide]
(V) (VIII)

In step a1 of Scheme I, an ester of formula (VI) is reduced according to the standard methods.

In step b1, the alcohol of formula (VII) thus obtained is reacted with 1H-isoindole-1,3-(2H)-dione to obtain the compound of formula (VIII). The reaction takes place in the presence of diethyl azodicarboxylate and triphenylphosphine, in a solvent such as tetrahydrofuran and at a temperature of between 0° C. and room temperature.

In step c1, the compound of formula (VIII) is reacted with hydrazine monohydrate in a solvent such as, for example, methanol or ethanol and at a temperature of between room temperature and the reflux temperature of the solvent.

The compounds of formula (VI) are commercial, known or prepared according to known methods.

The compounds of formula (I) according to the invention may contain one or more radioisotopes enabling their detection via diagnostic methods. These radioisotopes may be introduced via methods known to those skilled in the art, for instance those described in P. W. Miller et al. Angew. Chem. Int. Ed. Engl., (2008) 47, 8998-9033 or in F. Boisa et al. Nucl. Med. Biol. (2008) 35, 53-59, or in M. R. Zhang et al. Bioorg. Med. Chem. (2005) 13, 1811-1818.

The following Examples describe the preparation of certain compounds in accordance with the invention. These examples are not limiting and serve merely to illustrate the present invention The numbers of the compounds exemplified refer to those given in the Table below, which shows the chemical structures and the physical properties of some compounds according to the invention.

In the Preparations and in the Examples, the following abbreviations are used:
EtOAc: ethyl acetate,
BOC: tert-butyloxycarbonyl,
HPLC: high-performance liquid chromatography,
DCM: dichloromethane
DIPEA: diisopropylethylamine,
DMAP: 4-dimethylaminopyridine,
DME: 1,2-dimethoxyethane,
DMF: N,N-dimethylformamide,
DMSO: dimethyl sulfoxide
Ether: diethyl ether, 2N hydrochloric ether: 2N solution of hydrogen chloride in diethyl ether, iso ether: diisopropyl ether, m.p.: melting point, MeOH: methanol, pH 2 buffer solution: solution of 16.66 g of $KHSO_4$ and 32.22 g of $K_2SO_4$ in 1 liter of water,

RT: room temperature,

Tetrakis: tetrakis(triphenylphosphine)palladium,

TFA: trifluoroacetic acid,

THF: tetrahydrofuran.

The proton nuclear magnetic resonance spectra ($^1H$ NMR) are recorded at 200 MHz in DMSO-$d_6$. The chemical shifts δ are expressed in parts per million (ppm). For the interpretation of the spectra, the following abbreviations are used: s: singlet, d: doublet, t: triplet, quart: quartet, m: unresolved peak, mt: multiplet, bs: broad singlet, dd: doubled doublet.

The solvent mixtures are quantified in volumetric ratio.

The compounds according to the invention are analysed by LC/UV/MS coupling (liquid chromatography/UV detection/mass spectrometry). The molecular peak (MH$^+$) and the retention time (tr) in minutes are measured.

The conditions used are as follows:

Conditions M1

| | | | |
|---|---|---|---|
| An Acquity BEH $C_{18}$ (2.1 × 50 mm) 1.7 μm column is used; | | | |
| Eluent: | A: $H_2O$ + 0.05% TFA pH ≈ 3; acetonitrile (97/3); | | |
| | B: acetonitrile/0.035% TFA; | | |
| | Time (min) | % A | % B |
| Gradient: | 0 | 99 | 1 |
| | 2.3 | 5 | 95 |
| | 2.9 | 5 | 95 |
| | 3 | 99 | 1 |
| | 3.5 | 99 | 1 |
| Flow rate: | 1 ml/minute; | | |
| UV detection: | λ = 220 nm; | | |

Conditions M2

| | | |
|---|---|---|
| An X-Bridge $C_{18}$ (30 × 2.1 mm) 2.5 μm column is used; | | |
| Eluent: | A: $NH_4OAc$ 10 mM; pH ≈ 7; acetonitrile (97/3); | |
| | B: acetonitrile. | |
| | Time (min) | % A |
| Gradient: | 0 | 0 |
| | 4 | 100 |
| | 8 | 100 |
| | 8.1 | 0 |
| | 10 | 0 |
| Flow rate: | 0.8 ml/minute; | |
| UV detection: | λ = 220 nm; | |

The mass spectra are recorded in positive electrospray mode (ESI), in order to observe the ions derived from the protonation of the analysed compounds (MH$^+$) or from the formation of adducts with other cations such as N$^+$, K$^+$, etc.

PREPARATIONS

1. Preparation of the Compounds of Formula (V)

Preparation 1.1

2-[4-(Trifluoromethoxy)phenyl]ethanamine hydrochloride

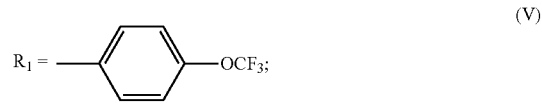

This compound is prepared according to the procedures described in step 1, Method A or Method B of Example 5 in WO 2006/044 732.

2. Preparation of the Compounds of Formula (II)

Preparation 2.1

4-Chloro-N-[2-(4-fluorophenyl)ethyl]-6-methoxy-1,3,5-triazin-2-amine

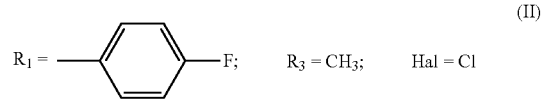

A solution of 10 g of 2,4-dichloro-6-methoxy-1,3,5-triazine in 200 ml of acetonitrile is cooled on an ice bath, 8.73 ml of DIPEA and then 6.56 ml of 2-(4-fluorophenyl)ethanamine are added and the mixture is stirred. The precipitate formed is drained by suction, washed with EtOAc and dried. 13.7 g of the expected compound are obtained.

Preparation 2.2

4-Chloro-N-{2-[4-(difluoromethoxy)phenyl]ethyl}-6-methoxy-1,3,5-triazin-2-amine

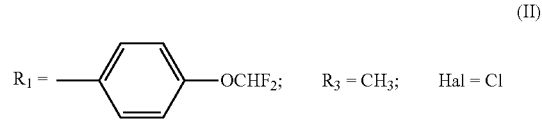

A solution of 1.8 g of 2,4-dichloro-6-methoxy-1,3,5-triazine in 40 ml of acetonitrile is cooled on an ice bath, 1.28 ml of DIPEA and then 1.68 g of 2-[4-(difluoromethoxy)phenyl]ethanamine are added and the mixture is stirred for 30 minutes. The reaction mixture is diluted by adding 100 ml of EtOAc and 50 ml of water, the phases are separated by settling, the organic phase is washed with saturated NaCl solution and dried over $MgSO_4$, and the solvent is evaporated off under vacuum. The residue is taken up in DCM, the insoluble matter is filtered off and the filtrate is concentrated under vacuum. The residue is chromatographed on silica gel, eluting with a cyclohexane/EtOAc mixture in a gradient of from (95/5 v/v) to (80/20 v/v). 0.94 g of the expected compound is obtained.

Preparation 2.3

4-Chloro-6-methoxy-N-{2-[4-(trifluoromethoxy)phenyl]ethyl}-1,3,5-triazin-2-amine

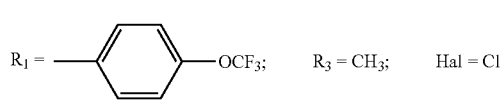

(II)

$R_1 =$ —⟨phenyl⟩—$OCF_3$; $R_3 = CH_3$; Hal = Cl

A solution of 5 g of 2,4-dichloro-6-methoxy-1,3,5-triazine in 50 ml of acetonitrile is cooled on an ice bath, 3.55 ml of DIPEA and then 5.13 g of 2-[4-(trifluoromethoxy)phenyl]ethanamine are added and the mixture is stirred for 30 minutes. The reaction mixture is partially concentrated under vacuum, an EtOAc/water mixture is added, the phases are separated by settling, the organic phase is washed with saturated NaCl solution and dried over $MgSO_4$, and the solvent is evaporated off under vacuum. The precipitate formed during the evaporation is drained by suction, washed with EtOAc and dried. 7.89 g of the expected compound are obtained.

3. Preparation of the compounds of formula (III)

Preparation 3.1

N-Cyclopropyl-2-methoxy-5-(4,4,5,5-tetramethyl-1,3,2-dioxaborolan-2-yl)benzenesulfonamide

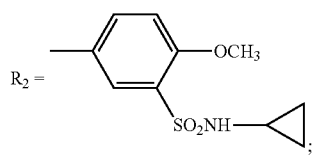

(III b)

A—5-Bromo-2-methoxybenzenesulfonyl chloride 10.7 ml of chlorosulfuric acid are cooled to 5-10° C., 6.7 ml of 1-bromo-4-methoxybenzene are added dropwise and the mixture is stirred for 1 hour at room temperature. The reaction mixture is poured onto ice, and the precipitate formed is drained by suction and washed with water. 9.8 g of the expected compound, of m.p.=105-107° C., are obtained.

B—5-Bromo-N-cyclopropyl-2-methoxybenzenesulfonamide

A solution of 0.49 g of cyclopropylamine in 20 ml of DCM is cooled to 0° C., the compound from the preceding step is added in 2-g portions and the mixture is stirred for 3 days at room temperature. The organic phase is washed with 10% HCl solution and with saturated NaCl solution and dried over $MgSO_4$, and the solvent is evaporated off under vacuum. The oil thus obtained is taken up in iso ether and the crystalline product formed is drained by suction. 1.32 g of the expected compound are obtained.

C—N-Cyclopropyl-2-methoxy-5-(4,4,5,5-tetramethyl-1,3,2-dioxaborolan-2-yl)benzenesulfonamide A mixture of 1.32 g of the compound from the preceding step, 1.31 g of 4,4,4',4',5,5,5',5'-octamethyl-2,2'-bi-1,3,2-dioxaborolane, 1.27 g of potassium acetate and 0.5 g of tetrakis(triphenylphosphine)palladium in 13 ml of DMF is heated at 80° C. for 24 hours. The reaction mixture is concentrated under vacuum, the residue is extracted with EtOAc and the organic phase is washed with a pH 2 buffer solution. The organic phase is filtered, the filtrate is dried over $MgSO_4$ and the solvent is evaporated off under vacuum. The residue is triturated from iso ether and the precipitate formed is drained by suction. 1.04 g of the expected compound are obtained.

Preparation 3.2

2-[3-(4,4,5,5-tetramethyl-1,3,2-dioxaborolan-2-yl)phenyl]propan-2-ol

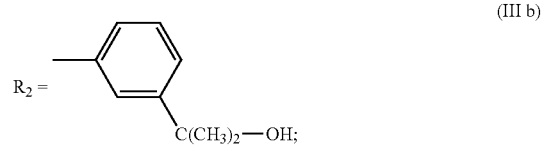

(III b)

$R_2 =$ —⟨phenyl⟩—$C(CH_3)_2$—OH;

A—2-(3-Bromophenyl)propan-2-ol

A solution of methylmagnesium iodide is prepared from 5.79 ml of methyl iodide and 2.2 g of magnesium turnings in refluxing ether. A solution of 5 g of methyl 3-bromobenzoate in 110 ml of ether is then added dropwise and the mixture is refluxed for 3 hours. The reaction mixture is poured onto ice/saturated $NH_4Cl$, the phases are separated by settling, the organic phase is washed with 10% $NaHCO_3$ solution and with saturated NaCl solution, and dried over $MgSO_4$, and the solvent is evaporated off under vacuum. 4.98 g of the expected compound are obtained.

B—2-[3-(4,4,5,5-tetramethyl-1,3,2-dioxaborolan-2-yl)phenyl]propan-2-ol

To a solution of 4.9 g of the compound from the preceding step in 100 ml of DMF are added 7.1 g of 4,4,4',4',5,5,5',5'-octamethyl-2,2'-bi-1,3,2-dioxaborolane, 6.7 g of potassium acetate and then 2.6 g of tetrakis(triphenylphosphine)palladium, and the mixture is heated at 120° C. for 3 hours. The reaction mixture is concentrated under vacuum, the residue is extracted with EtOAc, the organic phase is washed with water, with 10% $NaHCO_3$ solution and with saturated NaCl solution, and dried over $MgSO_4$, and the solvent is evaporated off under vacuum. The residue is chromatographed on silica gel, eluting with a cyclohexane/EtOAc mixture in a gradient of from (100/0 v/v) to (90/10 v/v). 4.3 g of the expected compound are obtained.

Preparation 3.3

2-[2-Chloro-5-(4,4,5,5-tetramethyl-1,3,2-dioxaborolan-2-yl)phenyl]propan-2-ol

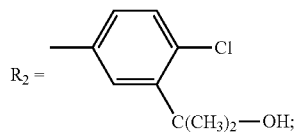

(III b)

A—2-(5-Bromo-2-chlorophenyl)propan-2-ol

A solution of methylmagnesium iodide is prepared from 2.02 ml of methyl iodide and 0.76 g of magnesium turnings in refluxing ether. A solution of 2 g of methyl 5-bromo-2-chlorobenzoate in 40 ml of ether is then added dropwise and the mixture is refluxed for 1 hour 30 minutes. The reaction mixture is poured onto ice/saturated NH$_4$Cl, the phases are separated by settling, the organic phase is washed with 10% NaHCO$_3$ solution and with saturated NaCl solution, and dried over MgSO$_4$, and the solvent is evaporated off under vacuum. 1.98 g of the expected compound are obtained in the form of an oil that crystallizes.

B—2-[2-Chloro-5-(4,4,5,5-tetramethyl-1,3,2-dioxaborolan-2-yl)phenyl]propan-2-ol

To a solution of 3 g of the compound from the preceding step in 60 ml of DMF are added 3.66 g of 4,4,4',4',5,5,5',5'-octamethyl-2,2'-bi-1,3,2-dioxaborolane, 3.54 g of potassium acetate and then 1.39 g of tetrakis(triphenylphosphine)palladium, and the mixture is heated at 60° C. for 12 hours. The reaction mixture is concentrated under vacuum, the residue is extracted with EtOAc, the organic phase is washed with water and filtered, the filtrate is dried over MgSO$_4$ and the solvent is evaporated off under vacuum. The residue is taken up in hot heptane, the tars are removed and the solvent is concentrated under vacuum. 3.1 g of the expected compound are obtained in the form of an oil that crystallizes.

Preparation 3.4

3-[3-(4,4,5,5-tetramethyl-1,3,2-dioxaborolan-2-yl)phenyl]pentan-3-ol

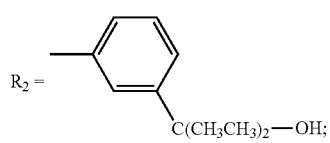

(III b)

A—3-(3-Bromophenyl)pentan-3-ol

A solution of ethylmagnesium iodide is prepared from 6.14 ml of ethyl iodide and 1.87 g of magnesium turnings in refluxing ether. A solution of 5 g of methyl 3-bromobenzoate in 110 ml of ether is then added dropwise and the mixture is refluxed for 2 hours 30 minutes. The reaction mixture is poured onto ice/saturated NH$_4$Cl, the phases are separated by settling, the organic phase is washed with 10% NaHCO$_3$ solution and with saturated NaCl solution, and dried over MgSO$_4$, and the solvent is evaporated off under vacuum. 6.3 g of the expected compound are obtained.

B—3-[3-(4,4,5,5-tetramethyl-1,3,2-dioxaborolan-2-yl)phenyl]pentan-3-ol

To a solution of 6.2 g of the compound from the preceding step in 100 ml of DMF are added 7.9 g of 4,4,4',4',5,5,5',5'-octamethyl-2,2'-bi-1,3,2-dioxaborolane, 7.5 g of potassium acetate and then 2.95 g of tetrakis(triphenylphosphine)palladium, and the mixture is heated at 120° C. for 3 hours 30 minutes. The reaction mixture is concentrated under vacuum, the residue is extracted with EtOAc, the organic phase is washed with water, with 10% NaHCO$_3$ solution and with saturated NaCl solution, and dried over MgSO$_4$, and the solvent is evaporated off under vacuum. The residue is chromatographed on silica gel, eluting with a cyclohexane/EtOAc mixture in a gradient of from (100/0 v/v) to (80/20 v/v). 3.3 g of the expected compound are obtained.

Preparation 3.5

[1-(tert-Butoxycarbonyl)-4-chloro-1H-indol-2-yl]boronic acid

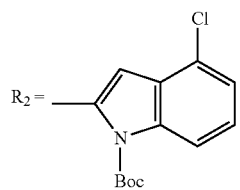

(III a)

A—tert-Butyl 4-chloro-1H-indole-1-carboxylate

To a solution of 3.6 g of 4-chloro-1H-indole in 20 ml of acetonitrile are added 5.7 g of di-tert-butyl dicarbonate and 0.03 g of DMAP, and the mixture is stirred overnight at room temperature. The reaction mixture is poured into a pH 2 buffer solution and extracted with EtOAc, the organic phase is washed with saturated NaCl solution and dried over MgSO$_4$, and the solvent is evaporated off under vacuum. 6 g of the expected compound are obtained.

B—[1-(tert-Butoxycarbonyl)-4-chloro-1H-indol-2-yl]boronic acid

A mixture of 1.5 g of the compound from the preceding step and 1.68 g of triisopropyl borate in 15 ml of THF is cooled to 0° C., followed by addition of 5.16 ml of a 1.5M solution of lithium diisopropylamide in THF, and the mixture is stirred for 1 hour while allowing the temperature to return to room temperature. The reaction mixture is acidified to pH 3-2 by addition of a pH 2 buffer solution and extracted with EtOAc, the organic phase is washed with saturated NaCl solution and dried over MgSO₄, and the solvent is evaporated off under vacuum. 1.68 g of the expected compound are obtained.

Preparation 3.6

[1-(tert-Butoxycarbonyl)-4-methoxy-1H-indol-2-yl]boronic acid

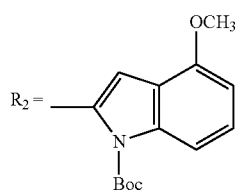

(III a)

A—1-[(E)-2-(2-methoxy-6-nitrophenyl)vinyl]pyrrolidine

To a solution of 10 g of 1-methoxy-2-methyl-3-nitrobenzene in 100 ml of DMF are added 8.74 ml of N,N-dimethylformamide dimethyl acetal and 5.44 ml of pyrrolidine, and the mixture is then refluxed for 3 hours. The mixture is concentrated to half its volume under vacuum, the remaining mixture is poured into ether/water and extracted with ether, the organic phase is washed with saturated NaCl solution and dried over MgSO₄, and the solvent is evaporated off under vacuum. 14.6 g of the expected compound are obtained in the form of a red oil.

B—4-Methoxy-1H-indole

Preparation of Activated Zinc Powder:

A suspension of 150 ml of zinc powder in 500 ml of 0.5N HCl is stirred for 1 hour at room temperature. The suspension is drained by suction, washed with water to neutral pH, with anhydrous EtOH and then with ether, and dried.

To a solution of 10 g of the compound from the preceding step in 46 ml of acetic acid are added, portionwise, 31.6 g of activated zinc, while keeping the temperature between 20 and 30° C. using an ice bath. The reaction mixture is stirred at room temperature for 30 minutes, and is filtered. The filtrate is extracted with EtOAc, the organic phase is washed with NaHCO₃ solution and with saturated NaCl solution, and dried over MgSO₄, and the solvent is evaporated off under vacuum. The residue is chromatographed on silica gel, eluting with a cyclohexane/EtOAc mixture in a gradient of from (98/2 v/v) to (95/5 v/v). 1.6 g of the expected compound are obtained.

C—tert-Butyl 4-methoxy-1H-indole-1-carboxylate

To a solution of 1.6 g of the compound from the preceding step in 20 ml of acetonitrile are added 2.6 g of di-tert-butyl dicarbonate and 0.03 g of DMAP, and the mixture is stirred overnight at room temperature. The reaction mixture is poured into a pH 2 buffer solution and extracted with EtOAc, the organic phase is washed with saturated NaCl solution and dried over MgSO₄, and the solvent is evaporated off under vacuum. The residue is chromatographed on silica gel, eluting with a cyclohexane/EtOAc mixture in a gradient of from (98/2 v/v) to (95/5 v/v). 2.4 g of the expected compound are obtained.

D—[1-(tert-Butoxycarbonyl)-4-methoxy-1H-indol-2-yl]boronic acid

A solution of 2.4 g of the compound from the preceding step and 2.74 g of triisopropyl borate in 25 ml of THF is cooled to 0° C., followed by addition of 8.41 ml of a 1.5N solution of lithium diisopropylamide, and the mixture is stirred for 1 hour while allowing the temperature to return to room temperature. The reaction mixture is acidified to pH 3-2 by addition of a pH 2 buffer solution and extracted with EtOAc, the organic phase is washed with saturated NaCl solution and dried over MgSO₄, and the solvent is evaporated off under vacuum. 2.7 g of the expected compound are obtained.

Preparation 3.7

[1-(tert-Butoxycarbonyl)-5-fluoro-1H-indol-2-yl]boronic acid

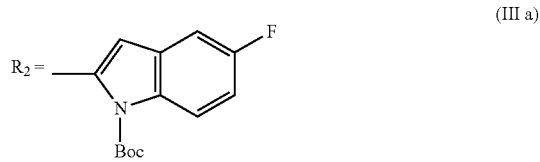 [SMILES: Cc1cc2cc(F)ccc2n1C(=O)OC(C)(C)C]

(III a)

This compound is prepared according to the procedure described in J. Org. Chem., 2002, 67, 7551-7552.

Preparation 3.8

2-Chloro-5-(4,4,5,5-tetramethyl-1,3,2-dioxaborolan-2-yl)phenol

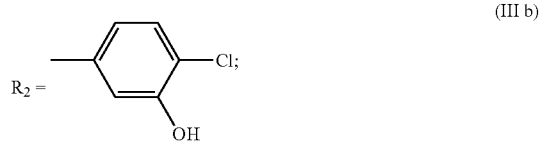

(III b)

To a solution of 5 g of 5-bromo-2-chlorophenol in 100 ml of DMF are added 7.5 g of 4,4,4',4',5,5,5',5'-octamethyl-2,2'-bi-1,3,2-dioxaborolane, 7.1 g of potassium acetate and then 1.97 g of tetrakis(triphenylphosphine)palladium, and the mixture is refluxed for 2 hours. The reaction mixture is concentrated under vacuum, the residue is extracted with EtOAc, the organic phase is washed with water, with 10% NaHCO₃ solution and with saturated NaCl solution, and dried over MgSO₄, and the solvent is evaporated off under vacuum. The residue is chromatographed on silica gel, eluting with a cyclohexane/EtOAc mixture in a gradient of from (100/0 v/v) to (80/20 v/v). 7 g of the expected compound are obtained.

Preparation 3.9

N-{3-[2-Chloro-5-(4,4,5,5-tetramethyl-1,3,2-dioxaborolan-2-yl)phenoxy]propyl}methanesulfonamide

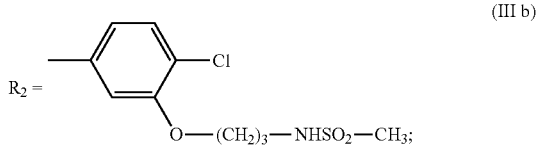

(III b)

A—2-[3-(5-Bromo-2-chlorophenoxy)propyl]-1H-isoindole-1,3 (2H)-dione

A suspension of 1.42 g of NaH at 60% in oil in 80 ml of DMF is cooled on an ice bath, a solution of 5 g of 5-bromo-2-chlorophenol in 80 ml of DMF is rapidly added dropwise, and the mixture is stirred for 15 minutes at room temperature. The reaction mixture is cooled on an ice bath, a solution of 9.7 g of 2-(3-bromopropyl)-1H-isoindole-1,3(2H)-dione in 80 ml of DMF is rapidly added dropwise, and the mixture is stirred overnight at room temperature. The solvent is partially concentrated under vacuum, water is added, the mixture is extracted with EtOAc, the organic phase is washed with saturated NaCl solution and dried over MgSO$_4$, and the solvent is evaporated off under vacuum. The residue is taken up in hot ether and stirred overnight at room temperature. The precipitate formed is drained by suction and washed with ether and then with pentane. 8.9 g of the expected compound are obtained.

B—3-(5-Bromo-2-chlorophenoxy)propan-1-amine

To a solution of 3 g of the compound obtained in the preceding step in 100 ml of 95% EtOH is added 0.75 ml of hydrazine monohydrate, and the mixture is refluxed for 4 hours. The reaction mixture is concentrated under vacuum, the residue is taken up in a DCM/10% NaOH mixture, the phases are separated by settling, the organic phase is washed with saturated NaCl solution and dried over MgSO$_4$, and the solvent is evaporated off under vacuum. The residue is taken up in ether and the precipitate formed is drained by suction. 1.75 g of the expected compound are obtained.

C—N-[3-(5-Bromo-2-chlorophenoxy)propyl]methanesulfonamide

To a solution of 1.7 g of the compound obtained in the preceding step in 15 ml of DCM are added 2.24 ml of triethylamine, and the solution is cooled on an ice bath. A solution of 0.55 ml of methanesulfonyl chloride in 0.5 ml of DCM is then added dropwise and the mixture is stirred for 1 hour at room temperature. The reaction mixture is extracted with DCM, the organic phase is washed with water, with a pH 2 buffer solution, with saturated NaCl solution and with saturated NaHCO$_3$ solution and dried over MgSO$_4$, and the solvent is evaporated off under vacuum. 2.4 g of the expected compound are obtained.

D—N-{3-[2-Chloro-5-(4,4,5,5-tetramethyl-1,3,2-dioxaborolan-2-yl)phenoxy]propyl}methanesulfonamide To a solution of 2.3 g of the compound from the preceding step in 60 ml of DMF are added 2.1 g of 4,4,4',4',5,5,5',5'-octamethyl-2,2'-bi-1,3,2-dioxaborolane, 1.98 g of potassium acetate and then 0.55 g of tetrakis(triphenylphosphine)palladium, and the mixture is refluxed for 2 hours 30 minutes. The reaction mixture is concentrated under vacuum, the residue is extracted with EtOAc, the organic phase is washed with water, with 10% NaHCO$_3$ solution and with saturated NaCl solution, and dried over MgSO$_4$, and the solvent is evaporated off under vacuum. The residue is chromatographed on silica gel, eluting with a cyclohexane/EtOAc mixture in a gradient of from (100/0 v/v) to (70/30 v/v). 1.8 g of the expected compound are obtained.

Preparation 3.10

2-[2-Methoxy-5-(4,4,5,5-tetramethyl-1,3,2-dioxaborolan-2-yl)phenyl]propan-2-ol

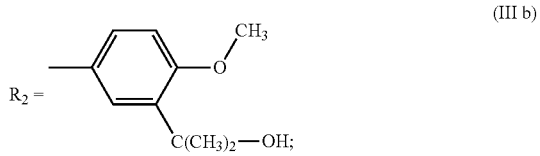

(III b)

A—Methyl 5-bromo-2-methoxybenzoate

To a solution of 5.0 g of 5-bromo-2-methoxybenzoic acid in 120 ml of MeOH are added a few drops of concentrated H$_2$SO$_4$, and the mixture is refluxed for 4 hours 30 minutes. The reaction mixture is concentrated under vacuum. 5.74 g of the expected compound are obtained, and are used without further purification.

B—2-(5-Bromo-2-methoxyphenyl)propan-2-ol

A solution of methylmagnesium iodide is prepared from 5.79 ml of methyl iodide and 2.2 g of magnesium turnings in refluxing ether. A solution of 5.7 g of the compound obtained in the preceding step in 110 ml of ether is then added dropwise and the mixture is refluxed for 2 hours. The reaction mixture is poured onto ice/saturated NH$_4$Cl, the phases are separated by settling, the organic phase is washed with 10% NaHCO$_3$ solution and with saturated NaCl solution, and dried over MgSO$_4$, and the solvent is evaporated off under vacuum. 5 g of the expected compound are obtained.

C—2-[2-Methoxy-5-(4,4,5,5-tetramethyl-1,3,2-dioxaborolan-2-yl)phenyl]propan-2-ol A solution of 4.9 g of the compound from the preceding step in 100 ml of DMF is sparged with nitrogen for 15 minutes, followed by addition of 6.21 g of 4,4,4',4',5,5,5',5'-octamethyl-2,2'-bi-1,3,2-dioxaborolane, 5.88 g of potassium acetate and then 2.31 g of tetrakis(triphenylphosphine)palladium, and the mixture is heated at 60° C. for 12 hours. The reaction mixture is concentrated under vacuum, the residue is extracted with EtOAc, the organic phase is washed with water, with saturated NaHCO$_3$ solution and with saturated NaCl solution, and dried over MgSO$_4$, and the solvent is evaporated off under vacuum. The residue is chromatographed on silica gel, eluting with a cyclohexane/EtOAc mixture. 2.47 g of the expected compound are obtained.

EXAMPLES

Example 1

Compound 1

N-[2-(4-Fluorophenyl)ethyl]-4-methoxy-6-(3-methoxyphenyl)-1,3,5-triazin-2-amine hydrochloride To a mixture of 0.5 g of the compound of Preparation 2.1 and 0.4 g of (3-methoxyphenyl)boronic acid in 24 ml of a toluene/EtOH mixture (3/1 v/v) are added 8 ml of 2M Na$_2$CO$_3$ solution and 0.4 g of tetrakis(triphenylphosphine) palladium, and the mixture is then refluxed for 3 hours. The reaction mixture is diluted by adding EtOAc, the organic phase is washed with water and with saturated NaCl solution and dried over Na$_2$SO$_4$, and the solvent is evaporated off under vacuum. The residue is chromatographed on silica gel, eluting with a cyclohexane/EtOAc mixture (70/30 v/v). The product obtained is dissolved in ether, a 2N hydrochloric ether solution is added dropwise, and the mixture is stirred for 15 minutes. The precipitate formed is drained by suction, washed and dried under vacuum. 0.13 g of the expected compound, of m.p.=194° C., is obtained.

Example 2

Compound 12

N-cyclopropyl-5(4-[[2-(4-fluorophenyl)ethyl] amino]-6-methoxy-1,3,5-triazin-2-yl)-2-methoxybenzenesulfonamide To a mixture of 0.3 g of the compound of Preparation 2.1 and 0.47 g of the compound of Preparation 3.1 in 10 ml of a DME/water mixture (80/20 v/v) are added 1.04 g of Cs$_2$CO$_3$ and 0.06 g of tetrakis(triphenylphosphine)palladium, and the mixture is stirred at room temperature. The reaction mixture is concentrated under vacuum, the residue is extracted with EtOAc, the organic phase is washed with a pH 2 buffer solution and with saturated NaCl solution, and dried over MgSO$_4$, and the solvent is evaporated off under vacuum. The residue is chromatographed on silica gel, eluting with a cyclohexane/EtOAc mixture in a gradient of from (100/0 v/v) to (50/50 v/v). 0.2 g of the expected compound, of m.p.=200-201° C., is obtained.

Example 3

Compound 18

4-(4-Chloro-1H-indol-2-yl)-N-[2-(4-fluorophenyl) ethyl]-6-methoxy-1,3,5-triazin -2-amine A—tert-Butyl 4-chloro-2-(4-{[2-(4-fluorophenyl) ethyl]amino}-6-methoxy-1,3,2-triazin-2-yl)-1H-indole-1-carboxylate To a mixture of 0.7 g of the compound of Preparation 2.1 and 0.8 g of the compound of Preparation 3.5 in 20 ml of a toluene/EtOH mixture (75/25 v/v) are added 9.9 ml of 2N Na$_2$CO$_3$ solution and then 0.029 g of tetrakis(triphenylphosphine)palladium, and the mixture is refluxed overnight. The reaction mixture is poured into ice/water and extracted with EtOAc, the organic phase is washed with saturated NaCl solution and dried over MgSO$_4$, and the solvent is evaporated off under vacuum. The residue is chromatographed on silica gel, eluting with an EtOAc/cyclohexane mixture in a gradient of from (2/98 v/v) to (5/95 v/v). 0.28 g of the expected compound is obtained.

B—4-(4-Chloro-1H-indol-2-yl)-N-[2-(4-fluorophenyl)ethyl]-6-methoxy-1,3,5-triazin-2-amine To a solution of 0.25 g of the compound from the preceding step in 5 ml of dioxane is added dropwise 0.38 ml of a 4N solution of HCl in dioxane, and the mixture is stirred for 3 hours at room temperature. The reaction mixture is concentrated under vacuum, the residue is taken up in 10 ml of DCM, 2.5 ml of TFA are added, and the mixture is stirred for 48 hours at room temperature. The reaction mixture is concentrated under vacuum, the residue is extracted with DCM, the organic phase is washed with NaHCO$_3$ solution and with water, and dried over MgSO$_4$, and the solvent is evaporated off under vacuum. The residue is chromatographed on silica gel, eluting with a DCM/MeOH mixture (98/2 v/v). 0.11 g of the expected compound is obtained.

Example 4

Compound 20

4-(5-Fluoro-1H-indol-2-yl)-N-[2-(4-fluorophenyl) ethyl]-6-methoxy-1,3,5-triazin -2-amine trifluoroacetate A—tert-Butyl 5-fluoro-2-(4-{[2-(4-fluorophenyl) ethyl]amino}-6-methoxy-1,3,5-triazin-2-yl)-1H-indole-1-carboxylate To a mixture of 0.5 g of the compound of Preparation 2.1 and 0.52 g of the compound of Preparation 3.7 in 50 ml of a DME/water mixture (70/30 v/v) are added 1.36 g of Cs$_2$CO$_3$ and 0.02 g of tetrakis(triphenylphosphine)palladium, and the mixture is refluxed for 12 hours. The reaction mixture is poured into ice/water and extracted with EtOAc, the organic phase is washed with saturated NaCl solution and dried over MgSO$_4$, and the solvent is evaporated off under vacuum. The residue is chromatographed on silica gel, eluting with a cyclohexane/EtOAc mixture in a gradient of from (98/2 v/v) to (90/10 v/v). 0.17 g of the expected compound is obtained.

B—4-(5-Fluoro-1H-indol-2-yl)-N-[2-(4-fluorophenyl)ethyl]-6-methoxy-1,3,5-triazin-2-amine trifluoroacetate To a solution of 0.17 g of the compound from the preceding step in 10 ml of dioxane is added dropwise 0.14 ml of TFA, and the mixture is stirred for 48 hours at room temperature. The reaction mixture is concentrated under vacuum, the residue is taken up in DCM and the solvent is evaporated off under vacuum. The residue is chromatographed on silica gel, eluting with a cyclohexane/EtOAc mixture in a gradient of from (98/2 v/v) to (90/10 v/v). 0.06 g of the expected compound, of m.p.=63° C., is obtained.

Example 5

Compound 46

2-{2-Chloro-5-[4-({2-[4-(difluoromethoxy)phenyl]ethyl}amino)-6-methoxy-1,3,5-triazin-2-yl]phenyl}propan-2-ol To a solution of 0.43 g of the compound of Preparation 2.2 in 10 ml of a DME/water mixture (80/20 v/v) are added 0.58 g of the compound of Preparation 3.3 and then 1.27 g of $Cs_2CO_3$ and 0.15 g of tetrakis(triphenylphosphine)palladium, and the mixture is stirred for 48 hours at room temperature. The reaction mixture is concentrated under vacuum, the residue is extracted with EtOAc, the organic phase is washed with a pH 2 buffer solution and with saturated NaCl solution, and dried over $MgSO_4$, and the solvent is evaporated off under vacuum. The residue is chromatographed on silica gel, eluting with cyclohexane and then with an EtOAc/cyclohexane mixture (60/40 v/v). 0.39 g of the expected compound, of m.p.=127° C., is obtained.

Example 6

Compound 56

2-[3-(4-{[2-(4-Fluorophenyl)ethyl]amino}-6-methoxy-1,3,5-triazin-2-yl)phenyl]propan-2-ol To a solution of 0.4 g of the compound of Preparation 2.1 in 10 ml of a DME/water mixture (80/20 v/v) are added 0.89 g of the compound of Preparation 3.2 and then 0.82 g of $Cs_2CO_3$ and 0.1 g of tetrakis(triphenylphosphine)palladium, and the mixture is refluxed for 5 hours. The reaction mixture is concentrated under vacuum, the residue is extracted with EtOAc, the organic phase is washed with saturated NaCl solution, and dried over $MgSO_4$, and the solvent is evaporated off under vacuum. The residue is chromatographed on silica gel, eluting with a cyclohexane/EtOAc mixture in a gradient of from (100/0 v/v) to (70/30 v/v). The product obtained is taken up in ether, and the precipitate formed is drained by suction, washed with ether and dried. 0.385 g of the expected compound is obtained.

Example 7

Compound 61

2-Chloro-5-(4-{[2-(4-fluorophenyl)ethyl]amino}-6-methoxy-1,3,5-triazin-2-yl)phenol To a solution of 0.5 g the compound of Preparation 2.1 in 10 ml of a DME/water mixture (80/20 v/v) are added 0.9 g of the compound of Preparation 3.8 and then 1.02 g of $Cs_2CO_3$ and 0.14 g of tetrakis(triphenylphosphine)palladium, and the mixture is refluxed for 3 hours 30 minutes. The reaction mixture is concentrated under vacuum, the residue is extracted with EtOAc, the organic phase is washed with saturated NaCl solution, and dried over $MgSO_4$, and the solvent is evaporated off under vacuum. The residue is chromatographed on silica gel, eluting with a cyclohexane/EtOAc mixture in a gradient of from (100/0 v/v) to (70/30 v/v). 0.630 g of the expected compound is obtained.

Example 8

Compound 63

Ethyl [2-chloro-5-(4-{[2-(4-fluorophenyl)ethyl]amino}-6-methoxy-1,3,5-triazin-2-yl)phenoxy]acetate To a mixture of 0.55 g of compound 61 and 0.22 g of $K_2CO_3$ in 15 ml of acetone is added 0.17 ml of ethyl bromoacetate, and the mixture is stirred for 5 hours at room temperature. The reaction mixture is concentrated under vacuum, the residue is extracted with EtOAc, the organic phase is washed with water and with saturated NaCl solution, and dried over $MgSO_4$, and the solvent is evaporated off under vacuum. The residue is chromatographed on silica gel, eluting with a cyclohexane/EtOAc mixture in a gradient of from (100/0 v/v) to (80/20 v/v). 0.5 g of the expected compound is obtained.

Example 9

Compound 65

2-[2-Chloro-5-(4-{[2-(4-fluorophenyl)ethyl]amino}-6-methoxy-1,3,5-triazin-2-yl)phenoxy]acetamide A—[2-Chloro-5-(4-{[2-(4-fluorophenyl)ethyl]amino}-6-methoxy-1,3,5-triazin-2-yl)phenoxy]acetic acid To a mixture of 0.2 g of compound 63 in 7 ml of THF are added 1 ml of water and then 0.02 g of lithium hydroxide monohydrate, and the mixture is stirred for 30 minutes. The reaction mixture is concentrated under vacuum, the residue is taken up in water and acidified by adding concentrated HCl, and the precipitate formed is drained by suction and dried under vacuum. 0.12 g of the expected compound is obtained.

B—2-[2-Chloro-5-(4-{[2-(4-fluorophenyl)ethyl]amino}-6-methoxy-1,3,5-triazin -2-yl)phenoxy]acetamide To a solution of 0.18 g of the compound from the preceding step in 5 ml of DMF are added 0.15 g of 1,1'-carbonyldiimidazole and then 0.4 ml of 20% aqueous ammonia solution, and the mixture is stirred for 24 hours at room temperature. The reaction mixture is concentrated under vacuum, the residue is extracted with EtOAc, the organic phase is washed with saturated $NaHCO_3$ solution, with saturated NaCl solution and with a pH 2 buffer solution, and dried over $MgSO_4$, and the solvent is evaporated off under vacuum. The residue is chromatographed on silica gel, eluting with DCM and then with a DCM/MeOH mixture in a gradient of from (98/2 v/v) to (90/10 v/v). 0.051 g of the expected compound is obtained.

Example 10

Compound 67

N-(3-{2-Chloro-5-[4-({2-[4-(difluoromethoxy)phenyl]ethyl}amino)-6-methoxy-1,3,5-triazin-2-yl]phenoxy}propyl)methanesulfonamide To a solution of 0.4 g of the compound of Preparation 2.2 in 10 ml of a DME/water mixture (80/20 v/v) are added 0.7 g of the compound of Preparation 3.9 and then 0.7 g of $Cs_2CO_3$ and 0.1 g of tetrakis(triphenylphosphine)palladium, and the mixture is refluxed for 2 hours 30 minutes. The reaction mixture is concentrated under vacuum, the residue is extracted with EtOAc, the organic phase is washed with saturated NaCl solution, and dried over MgSO₄, and the solvent is evaporated off under vacuum. The residue is chromatographed on silica gel, eluting with a cyclohexane/EtOAc mixture in a gradient of from (100/0 v/v) to (50/50 v/v). The product obtained is taken up in ether, and the precipitate formed is drained by suction, washed with ether and dried. 0.51 g of the expected compound is obtained.

Example 11

Compound 69

2-{2-Chloro-5-[4-({2-[4-(fluoromethoxy)phenyl]ethyl}amino)-6-methoxy-1,3,5-triazin-2-yl]phenyl}propan-2-ol A—4-(2-{[4-(4-Chlorophenyl)-6-methoxy-1,3,5-triazin-2-yl]amino}ethyl)phenol A suspension of 5 g of 2,4-dichloro-6-methoxy-1,3,5-triazine in 100 ml of acetonitrile is cooled on an ice bath, 4.89 ml of DIPEA are added dropwise, followed by addition of a solution of 3.85 g of 4-(2-aminoethyl)phenol in 50 ml of acetonitrile, and the mixture is stirred overnight at room temperature. The reaction mixture is concentrated under vacuum, the residue is extracted with EtOAc, the organic phase is washed with water and with saturated NaCl solution, and dried over MgSO₄, and the solvent is evaporated off under vacuum. The residue is taken up in iso ether and stirred while hot and then at room temperature, and the solid product is drained by suction and washed with iso ether. The product is chromatographed on silica gel, eluting with DCM and then with a DCM/MeOH mixture (90/10 v/v). 5.3 g of the expected compound are obtained.

B—4-[2-({4-[4-Chloro-3-(1-hydroxy-1-methylethyl)phenyl]-6-methoxy-1,3,5-triazin-2-yl}amino)ethyl]phenol To a solution of 2.5 g of the compound obtained in the preceding step in 50 ml of a DME/water mixture (80/20 v/v) are added 5.3 g of the compound of Preparation 3.3 and then 5.15 g of Cs₂CO₃ and 0.73 g of tetrakis(triphenylphosphine)palladium, and the mixture is refluxed for 2 hours 30 minutes. The reaction mixture is concentrated under vacuum, the residue is extracted with EtOAc, the organic phase is washed with saturated NaCl solution, and dried over MgSO₄, and the solvent is evaporated off under vacuum. The residue is chromatographed on silica gel, eluting with a cyclohexane/EtOAc mixture in a gradient of from (100/0 v/v) to (80/20 v/v). 2.8 g of the expected compound is obtained.

C—2-{2-Chloro-5-[4-({2-[4-(fluoromethoxy)phenyl]ethyl}amino)-6-methoxy-1,3,5-triazin-2-yl]phenyl}propan-2-ol A mixture of 0.3 g of the compound obtained in the preceding step, 0.15 g fluoromethyl 4-methylbenzenesulfonate and 0.47 g of Cs₂CO₃ in 4 ml of DMF is heated at 80° C. for 3 hours 30 minutes. The reaction mixture is concentrated under vacuum, the residue is extracted with EtOAc, the organic phase is washed with water and with saturated NaCl solution, and dried over MgSO₄, and the solvent is evaporated off under vacuum. The residue is chromatographed on silica gel, eluting with a cyclohexane/EtOAc mixture in a gradient of from (100/0 v/v) to (70/30 v/v). 0.2 g of the expected compound is obtained.

Table I that follows illustrates the chemical structures and physical properties of a number of examples of compounds according to the invention. In this table:

in the "Salt" column, "-" represents a compound in free base form, whereas "HCl" represents a compound in hydrochloride form;
Me represents a methyl radical;
iPr represents an isopropyl radical;
Et represents an ethyl radical.

TABLE 1

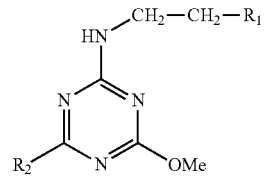

(I)

$R_3 = Me$

| Compounds No. | $R_1$ | $R_2$ | Salt MH⁺; tr (min) Conditions | IC50 (nM) hCB₂ |
|---|---|---|---|---|
| 1 | —⟨phenyl⟩—F | —⟨phenyl⟩—OMe | HCl 355; 1.73 M1 | 29.0 |

TABLE 1-continued
(I)
$R_3 = Me$
| Compounds No. | $R_1$ | $R_2$ | Salt MH$^+$; tr (min) Conditions | IC50 (nM) hCB$_2$ |
|---|---|---|---|---|
| 2 | 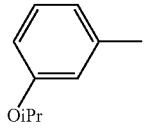 |  | — 383; 1.95 M1 | 39.0 |
| 3 | 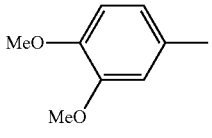 |  | — 385; 1.57 M1 | 11.0 |
| 4 | 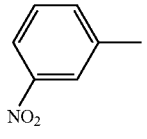 |  | — 370; 1.38 M1 | 29.0 |
| 5 | 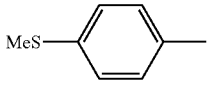 |  | — 371; 1.86 M1 | 14.0 |
| 6 | 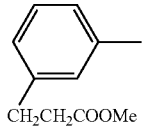 |  | — 411; 1.76 M1 | 12.0 |
| 7 | 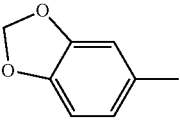 |  | — 369; 4.64 M2 | 9.0 |
| 8 | 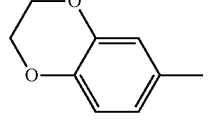 |  | — 383; 1.23 M1 | 14.0 |
| 9 | 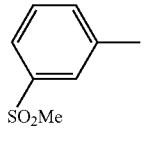 |  | — 403; 1.28 M1 | 38.0 |

TABLE 1-continued
R₃ = Me
| Compounds No. | R₁ | R₂ | Salt MH⁺; tr (min) Conditions | IC50 (nM) hCB₂ |
|---|---|---|---|---|
| 10 | 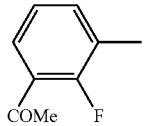 |  | — 385; 1.32 M1 | 10.0 |
| 11 | 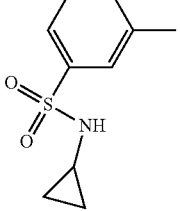 |  | — 444; 1.31 M1 | 2.7 |
| 12 | 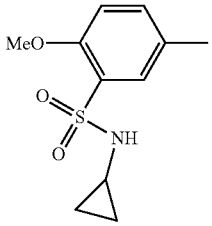 |  | — 474; 1.92 M1 | 12.0 |
| 13 | 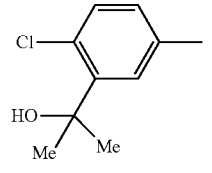 |  | — 417; 2.15 M1 | 0.4 |
| 14 | 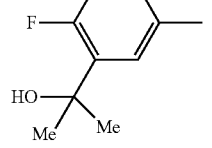 |  | — 401; 1.82 M1 | 8.0 |
| 15 | 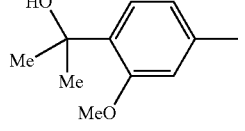 |  | — 413; 1.95 M1 | 17.0 |
| 16 | 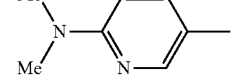 | (Me)(Me)N-pyridyl-Me | — 369; 1.02 M1 | 35.0 |

TABLE 1-continued
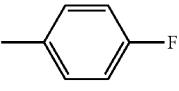
R₃ = Me
| Compounds No. | R₁ | R₂ | Salt MH⁺; tr (min) Conditions | IC50 (nM) hCB₂ |
|---|---|---|---|---|
| 17 | 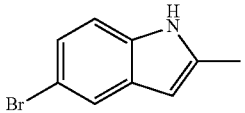 |  | HCl 442; 1.95 M1 | 17.0 |
| 18 | 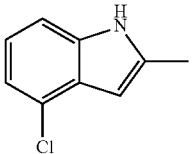 |  | — 398; 1.92 M1 | 7.0 |
| 19 | 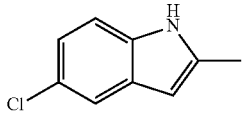 |  | HCl 398; 1.91 M1 | 14.0 |
| 20 | 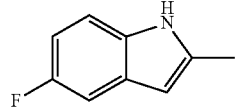 |  | TFA 382; 1.77 M1 | 12.0 |
| 21 | 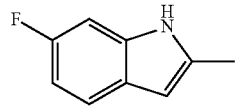 | 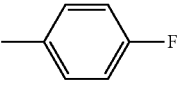 | TFA 382; 2.07 M1 | 48.0 |
| 22 | 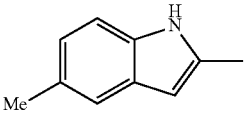 | 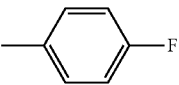 | — 378; 1.87 M1 | 24.0 |
| 23 | 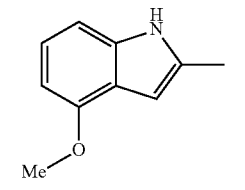 | 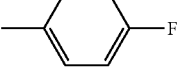 | TFA 394; 1.70 M1 | 33.0 |
| 24 | 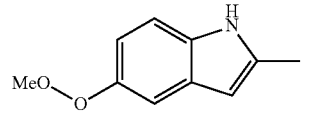 | | TFA 394; 1.67 M1 | 21.0 |

TABLE 1-continued
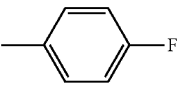
R$_3$ = Me
| Compounds No. | R$_1$ | R$_2$ | Salt MH$^+$; tr (min) Conditions | IC50 (nM) hCB$_2$ |
|---|---|---|---|---|
| 25 | 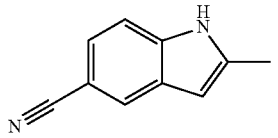 |  | HCl 389; 1.72 M1 | 27.0 |
| 26 | 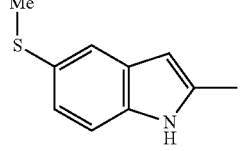 |  | — 410; 4.00 M2 | 37.0 |
| 27 | 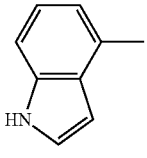 | 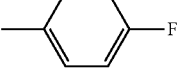 | — 364; 4.62 M2 | 27.0 |
| 28 | 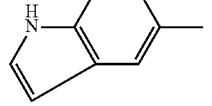 | 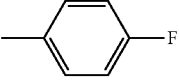 | — 364; 4.62 M2 | 34.0 |
| 29 | 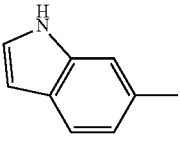 | 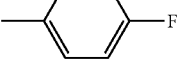 | — 364; 1.19 M1 | 14.0 |
| 30 | 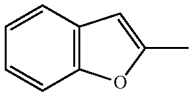 | 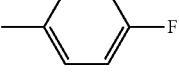 | — 365; 1.37 M1 | 5.0 |
| 31 | 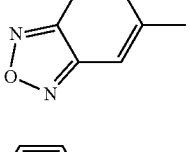 | 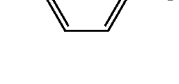 | — 367; 1.39 M1 | 42.0 |
| 32 | 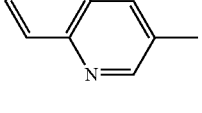 |  | — 376; 4.67 M2 | 34.0 |

TABLE 1-continued
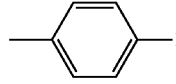
(I)
R₃ = Me
| Compounds No. | R₁ | R₂ | Salt MH⁺; tr (min) Conditions | IC50 (nM) hCB₂ |
|---|---|---|---|---|
| 33 | 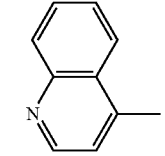 | 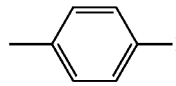 | — 376; 1.14 M1 | 11.0 |
| 34 | 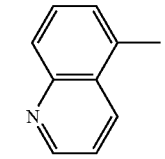 | 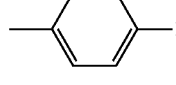 | — 376; 3.98 M2 | 47.0 |
| 35 | 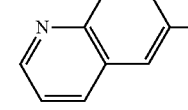 | 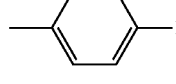 | — 376; 4.32 M2 | 32.0 |
| 36 | 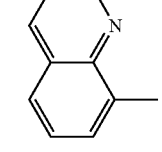 | 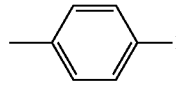 | — 376; 0.98 M1 | 17.0 |
| 37 | 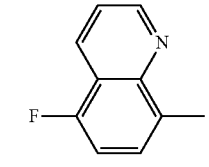 | 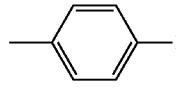 | — 394; 1.59 M1 | 1.0 |
| 38 | 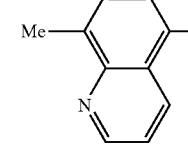 | 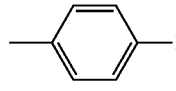 | — 390; 1.19 M1 | 38.0 |
| 39 | 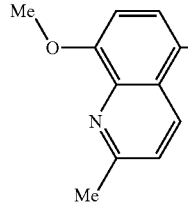 |  | — 420; 1.02 M1 | 38.0 |

TABLE 1-continued
(I)
R₃ = Me
| Compounds No. | R₁ | R₂ | Salt MH⁺; tr (min) Conditions | IC50 (nM) hCB₂ |
|---|---|---|---|---|
| 40 | 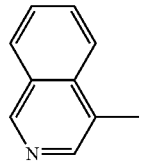 | 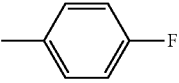 | — 376; 3.58 M2 | 21.0 |
| 41 | 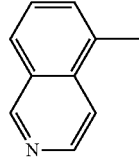 | 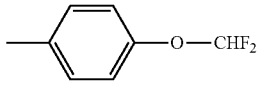 | — 376; 1.04 M1 | 20.0 |
| 42 | 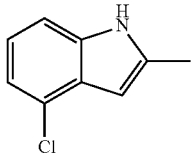 | 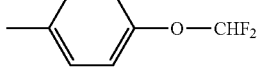 | TFA 446; 1.92 M1 | 24.0 |
| 43 | 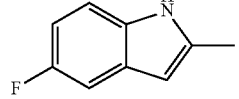 | 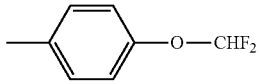 | HCl 430; 1.79 M1 | 45.0 |
| 44 | 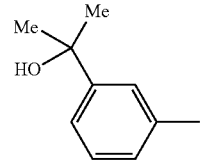 | 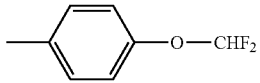 | — 431; 1.90 M1 | 18.0 |
| 45 | 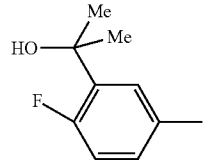 | 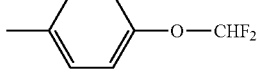 | — 449; 1.84 M1 | 30.0 |
| 46 | 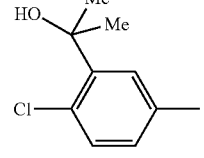 |  | — 465; 2.15 M1 | 1.2 |

TABLE 1-continued
(I)
$R_3 = Me$
| Compounds No. | $R_1$ | $R_2$ | Salt MH$^+$; tr (min) Conditions | IC50 (nM) hCB$_2$ |
|---|---|---|---|---|
| 47 | 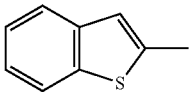 |  | — 381; 2.28 M1 | 4.0 |
| 48 | 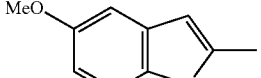 | 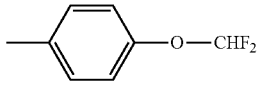 | — 395; 2.06 M1 | 12.0 |
| 49 | 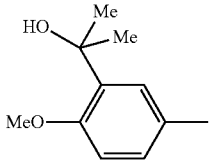 | 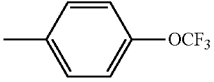 | — 461; 1.92 M1 | 4.0 |
| 50 | 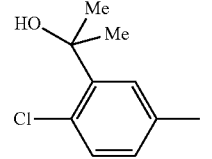 |  | — 483; 2.28 M1 | 12.0 |
| 51 | 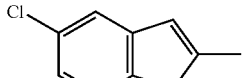 |  | 399; 2.25 M1 | 23.0 |
| 52 | 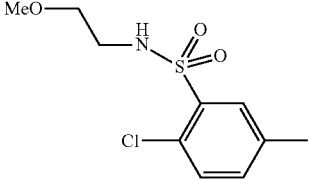 |  | — 495; 1.98 M1 | 42.0 |
| 53 | 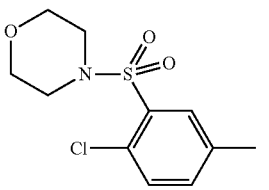 |  | — 507; 2.09 M1 | 3.0 |

TABLE 1-continued
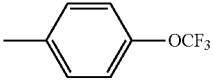
(I)
R₃ = Me
| Compounds No. | R₁ | R₂ | Salt MH⁺; tr (min) Conditions | IC50 (nM) hCB₂ |
|---|---|---|---|---|
| 54 | 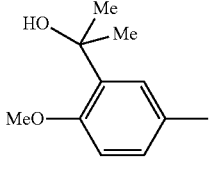 | 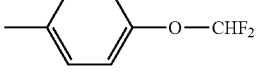 | — 479; 2.07 M1 | 9.0 |
| 55 | 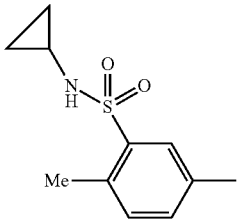 |  | — 506; 2.02 M1 | 44.0 |
| 56 | 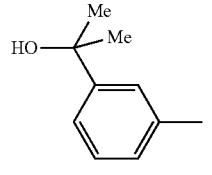 | 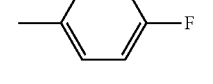 | — 383; 1.86 M1 | 9.0 |
| 57 | 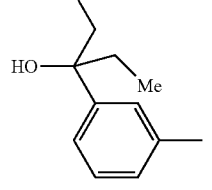 | 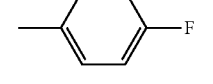 | — 411; 2.08 M1 | 21.0 |
| 58 | 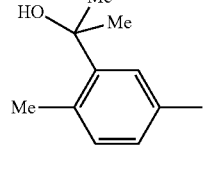 | 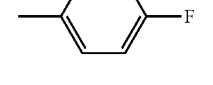 | — 413; 1.89 M1 | 1.0 |
| 59 | | 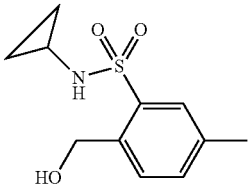 | — 474; 1.82 M1 | 25.0 |

TABLE 1-continued (I)

R₃ = Me

| Compounds No. | R₁ | R₂ | Salt MH⁺; tr (min) Conditions | IC50 (nM) hCB₂ |
|---|---|---|---|---|
| 60 | -C₆H₄-O-CHF₂ (4-) | 3-methyl-N-cyclopropyl-benzenesulfonamide | — 492; 3.71 M2 | 23.0 |
| 61 | 4-F-C₆H₄- | 2-chloro-5-methyl-phenol (HO-) | — 375; 3.72 M2 | 21.0 |
| 62 | 4-F-C₆H₄- | 2-chloro-5-methyl-N-cyclopropyl-benzenesulfonamide | — 478; 2.05 M1 | 4.0 |
| 63 | 4-F-C₆H₄- | ethyl 2-(2-chloro-5-methylphenoxy)acetate | — 461; 2.21 M1 | 10.0 |
| 64 | 4-F-C₆H₄- | 2-methoxy-5-methyl-benzonitrile | — 380; 2.02 M1 | 19.0 |

TABLE 1-continued
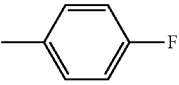
(I)
$R_3 = Me$
| Compounds No. | $R_1$ | $R_2$ | Salt MH⁺; tr (min) Conditions | IC50 (nM) hCB₂ |
|---|---|---|---|---|
| 65 | 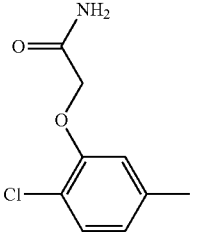 | 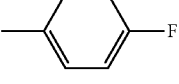 | —<br>432; 3.55<br>M2 | 1.0 |
| 66 | 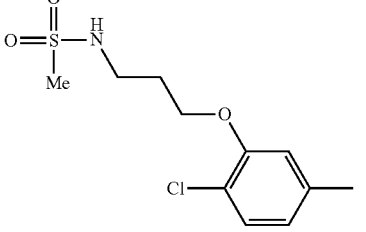 | 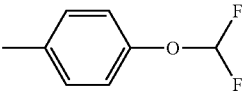 | —<br>510; 2.02<br>M1 | 18.0 |
| 67 | 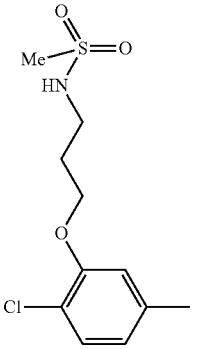 | 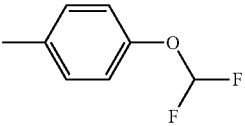 | —<br>558; 2.03<br>M1 | 41.0 |
| 68 | 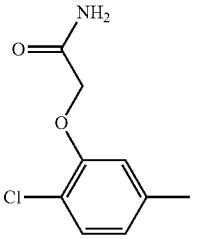 |  | —<br>480; 3.01<br>M1 | 11.0 |

TABLE 1-continued (I)

Structure: R₂ and HN-CH₂-CH₂-R₁ groups attached to 1,3,5-triazine ring with OMe group. R₃ = Me

| Compounds No. | R₁ | R₂ | Salt MH⁺; tr (min) Conditions | IC50 (nM) hCB₂ |
|---|---|---|---|---|
| 69 | 4-(fluoromethoxymethyl)phenyl (—C₆H₄—O—CH₂—F) | 2-(1-hydroxy-1-methylethyl)-4-methyl-phenyl with Cl (HO-C(Me)₂-, Cl, Me substituted phenyl) | 447; 2.07 M1 | 3.9 |
| 70 | 4-(fluoromethoxymethyl)phenyl | 2-(1-hydroxy-1-methylethyl)-4-methyl-phenyl with OMe substituent | 443; 1.83 M1 | 9.0 |

Example 12

Compound 71

2-{2-Chloro-5-[4-(fluoromethoxy)-6-{[2-(4-fluorophenyl)ethyl]amino}-1,3,5-triazin-2-yl]phenyl}propan-2-ol A—4-[4-Chloro-3-(1-hydroxy-1-methylethyl)phenyl]-6-{[2-(4-fluorophenyl)ethyl]amino}-1,3,5-triazin-2-ol To 27.43 ml of a 25% by weight solution of sodium methoxide in MeOH are added 1 g of compound 13 and 20 ml of MeOH, and the mixture is then refluxed for 5 hours. The reaction mixture is concentrated under vacuum, the residue is extracted with EtOAc, the organic phase is washed with water, with a pH 2 buffer solution, with saturated NaCl solution, with saturated NaHCO₃ solution and with saturated NaCl solution and dried over MgSO₄, and the solvent is evaporated off under vacuum. The residue is chromatographed on silica gel, eluting with DCM and then with a DCM/MeOH mixture (95/5 v/v). 0.47 g of the expected compound is obtained.

B—tert-Butyl {4-[4-chloro-3-(1-hydroxy-1-methylethyl)phenyl]-6-hydroxy-1,3,5-triazin-2-yl}[2-(4-fluorophenyl)ethyl]carbamate To a mixture of 0.47 g of the compound obtained in the preceding step in 15 ml of THF are added 0.37 g of di-tert-butyl dicarbonate and then 0.72 g of Cs₂CO₃, and the mixture is stirred for 3 hours 30 minutes at room temperature. The reaction mixture is then refluxed for 4 hours and concentrated under vacuum. The residue is extracted with EtOAc, the organic phase is washed with water and with saturated NaCl solution, and dried over MgSO₄, and the solvent is evaporated off under vacuum. The residue is chromatographed on silica gel, eluting with cyclohexane and then with a cyclohexane/EtOAc mixture (60/40 v/v). 0.3 g of the expected compound is obtained.

C—tert-Butyl {4-[4-chloro-3-(1-hydroxy-1-methylethyl)phenyl]-6-(fluoromethoxy)-1,3,5-triazin-2-yl}[2-(4-fluorophenyl)ethyl]carbamate A mixture of 0.17 g of the compound obtained in the preceding step, 0.1 g fluoromethyl 4-methylbenzenesulfonate and 0.22 g of Cs₂CO₄ in 4 ml of DMF is heated at 100° C. for 4 hours in a sealed tube. The reaction mixture is concentrated under vacuum, the residue is extracted with EtOAc, the organic phase is washed with water and with saturated NaCl solution, and dried over MgSO₄, and the solvent is evaporated off under vacuum. The residue is chromatographed on silica gel, eluting with a cyclohexane/EtOAc mixture in a gradient of from (100/0 v/v) to (90/10 v/v). 0.12 g of the expected compound is obtained.

D—2-{2-Chloro-5-[4-(fluoromethoxy)-6-{[2-(4-fluorophenyl)ethyl]amino}-1,3,5-triazin-2-yl]phenyl}propan-2-ol To a solution of 0.12 g of the compound from the preceding step in 3 ml of DCM is added dropwise 0.09 ml of TFA, and the mixture is stirred overnight at room temperature. 0.09 ml of TFA is added and the mixture is heated at 30° C. for 8 hours. The reaction mixture is concentrated under vacuum. The residue is chromatographed on silica gel, eluting with cyclohexane and then with a cyclohexane/EtOAc mixture (80/20 v/v). 0.095 g of the expected compound is obtained.

MH⁺=435; tr=2.16 min (Method M1).

IC50 on hCB₂=1.2 nM.

Example 13

Compound 58

2-[5-(4-{[2-(4-Fluorophenyl)ethyl]amino}-6-methoxy-1,3,5-triazin-2-yl)-2-methoxyphenyl]propan-2-ol Nitrogen is sparged for 15 minutes through a mixture of 1.0 g of the compound of Preparation 2.1, 1.42 g of the compound of Preparation 3.10 and 3.46 g of $Cs_2CO_3$ in 50 ml of a DME/water mixture (80/20 v/v). 0.73 g of 1,1'-bis(diphenylphosphino)ferrocenepalladium(II) dichloride complex with dichloromethane is then added and the mixture is refluxed for 3 hours. The reaction mixture is filtered through Celite® and the filtrate is concentrated under vacuum. The residue is extracted with EtOAc, the organic phase is washed with water and with saturated NaCl solution, and dried over $MgSO_4$, and the solvent is evaporated off under vacuum. The residue is chromatographed on silica gel, eluting with a cyclohexane/EtOAc mixture in a gradient of from (100/0 v/v) to (90/10 v/v). 1.1 g of the expected compound is obtained.

Example 14

Compound 72

2-{5-[4-(Fluoromethoxy)-6-{[2-(4-fluorophenyl)ethyl]amino}-1,3,5-triazin-2-yl]-2-methoxyphenyl}propan-2-ol A—4-{[2-(4-Fluorophenyl)ethyl]amino}-6-[3-(1-hydroxy-1-methylethyl)-4-methoxyphenyl]-1,3,5-triazin-2-ol.

To 12 ml of a 25% by weight solution of sodium methoxide in MeOH are added 1.1 g of compound 58 and 20 ml of MeOH, and the mixture is then refluxed for 10 days. The reaction mixture is concentrated under vacuum, the residue is extracted with EtOAc, the organic phase is washed with water, with a pH 2 buffer solution and with saturated NaCl solution and dried over $MgSO_4$, and the solvent is evaporated off under vacuum. The aqueous phase is recovered and the precipitate formed is drained by suction and washed with water and then with EtOAc. 1.0 g of the expected compound is obtained.

B—tert-Butyl [2-(4-fluorophenyl)ethyl]{4-hydroxy-6-[3-(1-hydroxy-1-methylethyl)-4-methoxyphenyl]-1,3,5-triazin-2-yl}carbamate To a mixture of 1 g of the compound obtained in the preceding step in 30 ml of THF are added 0.85 g of di-tert-butyl dicarbonate and then 1.64 g of $Cs_2CO_3$, and the mixture is stirred for 2 days at room temperature. The reaction mixture is then refluxed for 2 hours and concentrated under vacuum. The residue is extracted with EtOAc, the organic phase is washed with water and with saturated NaCl solution, and dried over $MgSO_4$, and the solvent is evaporated off under vacuum. The residue is chromatographed on silica gel, eluting with a cyclohexane/EtOAc mixture in a gradient of from (100/0 v/v) to (0/100 v/v). 0.82 g of the expected compound is obtained.

C—tert-Butyl {4-(Fluoromethoxy)-6-[3-(1-hydroxy-1-methylethyl)-4-methoxyphenyl]-1,3,5-triazin-2-yl}[2-(4-fluorophenyl)ethyl]carbamate To a solution of 0.3 g of the compound from the preceding step in 6 ml of DMF is added portionwise 0.0265 g of NaH at 60% in oil, and the mixture is stirred for 15 minutes at room temperature. The reaction mixture is cooled on an ice bath, 0.227 g of chlorofluoromethane is introduced by sparging over 5 minutes, and the flask is hermetically sealed and heated at 80° C. for 1 hour. The reaction mixture is concentrated under vacuum, the residue is extracted with ether, the organic phase is washed with water and with saturated NaCl solution, and dried over $MgSO_4$, and the solvent is evaporated off under vacuum. The residue is chromatographed on silica gel, eluting with a cyclohexane/EtOAc mixture in a gradient of from (100/0 v/v) to (60/40 v/v). 0.27 g of the expected compound is obtained.

D—2-{5-[4-(Fluoromethoxy)-6-{[2-(4-fluorophenyl)ethyl]amino}-1,3,5-triazin-2-yl]-2-methoxyphenyl}propan-2-ol To a solution of 0.34 g of the compound from the preceding step in 6 ml of DCM is added 0.25 ml of TFA, and the mixture is stirred for 5 hours at room temperature. The reaction mixture is diluted by adding DCM, the organic phase is washed with water, with saturated $N_aHCO^3$ solution and with saturated NaCl solution and dried over $_{Mg}SO_4$, and the solvent is evaporated off under vacuum. The residue is chromatographed on silica gel, eluting with a cyclohexane/EtOAc mixture in a gradient of from (100/0 v/v) to (70/30 v/v). 0.15 g of the expected compound is obtained.

$MH^+$=431; tr=1.99 min (Method M1).

IC50 on hCB2=1.2 nM.

The compounds according to the invention showed very good in vitro affinity (IC50<50 nM) for human $CB_2$ receptors and also good selectivity towards human $CB_1$ receptors. Affinity binding tests were performed according to the experimental conditions described by M. Rinaldi-Carmona in J. Pharmacol. Exp. Therap. 1998, 287, 644-650, with membranes derived either from rodent tissues or from recombinant cell lines in which the human $CB_2$ receptors were expressed (Munro et al., Nature 1993, 365, 61-65). The affinity of the compounds is expressed in the form of the IC50 (concentration causing 50% inhibition of specific binding of the tritiated ligand used in vitro). The results obtained for each compound on the human $CB_2$ receptors are indicated in Table I.

The compounds according to the invention showed a modulatory effect on the $CB_2$ receptors. In particular, the compounds according to the invention have properties of agonist, inverse agonist and/or antagonist nature.

The agonist nature of the compounds according to the invention was demonstrated in models of adenylate cyclase inhibition (stimulated with forskolin) as described in M. Rinaldi-Carmona et al., J. Pharmacol. Exp. Ther. 1996, 278, 871-878 and 1998, 284, 644-650 and M Bouaboula et al., J. Biol Chem., 1997, 272, 22330-22339.

The antagonist nature of the compounds according to the invention was demonstrated in models of reversion of adenylate cyclase inhibition (stimulated with forskolin) induced by a $CB_2$ receptor agonist, as described in M. Rinaldi-Carmona et al., J. Pharmacol. Exp. Ther. 1996, 278, 871-878 and 1998, 284, 644-650.

The inverse agonist nature of the compounds according to the invention was demonstrated in models of adenylate cyclase activation (stimulated with forskolin) as described in M. Portier et al., J. Pharmacol. Exp. Ther. 1999, 288, 582-589.

The compounds according to the invention are capable of penetrating into the brain, after intravenous or oral administration. The penetration of the compounds into the brain was demonstrated by pharmacokinetic study, by assaying the amount of product present in the brain after intravenous or oral administration to mice.

The compounds according to the invention, in cold or radiolabelled form, may be used as pharmacological tools or as diagnostic tools in man or animals, for detecting and labelling the $CB_2$ cannabinoid receptors Thus, according to one of its aspects, the present invention relates to a compound of formula (I) containing one or more isotopes that are compatible with its use as a marker in positron emission tomography (PET) or single-photon emission tomography (SPECT) imaging, for instance carbon-11, fluorine-18 or iodine-123, for the diagnosis of diseases associated with overexpression of the $CB_2$ receptors. Examples that may be mentioned include diseases associated with neuroinflammation such as Alzheimer's disease, Huntington's chorea, amyotrophic lateral sclerosis, multiple sclerosis, HIV-related encephalopathy, ischaemia, stroke and Parkinson's disease, but also peripheral diseases in which the $CB_2$ receptor is involved, such as atherosclerosis, endometrial inflammation, fibroses, in particular liver fibrosis, chronic liver diseases of alcoholic origin, cirrhosis, viral and toxic diseases, and also steatohepatitis of non-alcoholic origin and primary liver cancer.

Furthermore, the compounds of the present invention are especially active principles that are compatible with their use as medicaments and/or pharmaceutical compositions.

According to another of its aspects, the present invention relates to a compound of formula (I) or a pharmaceutically acceptable salt thereof, for preventing and/or treating any human pathology and/or for veterinary use. Thus, the compounds according to the invention may be used on man or animals (especially mammals including, in a non-limiting manner, dogs, cats, horses, cattle and sheep), for preventing or treating diseases involving the $CB_2$ receptors.

Mention may be made, for example, of the following diseases or complaints:
- immune system disorders: especially autoimmune diseases including, in a non-exhaustive manner: psoriasis, lupus erythematosus, connective tissue diseases, Sjögrer's syndrome, ankylosing spondylitis, rheumatoid arthritis, reactive arthritis, undifferentiated spondylitis, Charcot's disease, Behçet's disease, haemolytic autoimmune anaemias, multiple sclerosis, amyotrophic lateral sclerosis, amylosis, graft rejection, diseases affecting the plasmocytic line;
- allergic diseases: especially immediate or delayed hypersensitivity, asthma, allergic rhinitis, contact dermatitis and allergic conjunctivitis;
- parasitic, viral or bacterial infectious diseases especially including AIDS and meningitis;
- amylosis and diseases affecting the lympho-haematopoietic system;
- chronic liver diseases of alcoholic origin, cirrhosis, viral and toxic diseases, and also steatohepatitis of non-alcoholic origin and primary liver cancer;
- inflammatory diseases: especially articular diseases: arthritis, rheumatoid arthritis, osteoarthritis, spondylitis, gout, vascularitis, Crohn's disease, irritable bowel syndrome (IBS), inflammatory bowel disease (IBD), ulcerative colitis and acute pancreatitis;
- bone diseases and osteoporosis;
- pain: especially chronic pain of inflammatory type, neuropathic pain and acute peripheral pain;
- ocular complaints: especially ocular hypertension and glaucoma;
- pulmonary complaints: respiratory pathway diseases, asthma, chronic bronchitis, chronic obstructive pulmonary disease (COPD), emphysema;
- central nervous system diseases and neurodegenerative diseases: especially Tourette's syndrome, Parkinson's disease, Alzheimer's disease, senile dementia, chorea, Huntington's chorea, epilepsy, psychoses, depression and spinal cord lesions;
- migraine, stress, diseases of psychosomatic origin, panic attacks, epilepsy, movement disorders, dizziness, vomiting, nausea, in particular subsequent to chemotherapy;
- cardiovascular diseases, in particular hypertension, arterial sclerosis, heart attack and cardiac ischaemia;
- renal ischaemia;
- cancers: especially benign skin tumours, papillomas and cancerous tumours, prostate tumours, cerebral tumours (examples: glioblastomas, medulloepitheliomas, medulloblastomas, neuroblastomas, tumours of embryonic origin, astrocytomas, astroblastomas, ependymomas, oligodendrogliomas, plexus tumour, neuroepitheliomas, tumour of the pineal gland, ependymoblastomas, neuroectodermic tumours, malignant meningiomas, sarcomatoses, malignant melanomas, schwennomas);
- gastrointestinal disorders, diarrheal disorders, ulcers, bladder and urinary disorders, nephritis, disorders of endocrine origin, haemorrhagic shock, septic shock, Reynaud's disease and fertility disorders;
- obesity; type II diabetes, metabolic syndrome, insulin resistance and adipose tissue inflammation;
- fibroses: pulmonary, renal, hepatic and dermal.

More particularly, the compounds of formula (I) according to the present invention will be useful for preventing and/or treating pain, inflammatory diseases, autoimmune diseases, allergic diseases, infectious diseases, neurodegenerative diseases, cardiovascular diseases, cancers, gastrointestinal diseases, obesity, type II diabetes, insulin resistance, adipose tissue inflammation and fibrosis.

The use of the compounds according to the invention for preventing and/or treating the diseases mentioned above, and also for preparing medicaments intended for treating these diseases, forms an integral part of the invention.

The compounds of formula (I) above, or a pharmaceutically acceptable salt thereof, may be used at daily doses of from 0.01 to 100 mg per kg of body weight of the mammal to be treated, and preferably at daily doses of from 0.1 to 50 mg/kg. In the case of humans, the dose may preferably range from 0.1 to 4000 mg per day and more particularly from 0.5 to 1000 mg depending on the age of the individual to be treated or the type of treatment: prophylactic or curative.

Thus, according to another of its aspects, the present invention relates to pharmaceutical compositions containing, as active principle, a compound of formula (I), or a pharmaceutically acceptable salt thereof, and also one or more pharmaceutically acceptable excipients.

In the pharmaceutical compositions of the present invention for oral, sublingual, inhaled, subcutaneous, intramuscular, intravenous, topical, intratracheal, intranasal, transdermal, local or rectal administration, the active principles may be administered in unit administration forms, as a mixture with standard pharmaceutical supports, to man and animals.

The appropriate unit administration forms comprise oral-route forms such as tablets, soft or hard gel capsules, powders, granules or oral solutions or suspensions, sublingual, buccal, intratracheal, intraocular or intranasal administration forms, inhalation forms, aerosols, topical or transdermal administration forms, implants, subcutaneous, intramuscular or intravenous administration forms and rectal administration forms.

For topical administration, the compounds according to the invention may be used in creams, pomades, gels or lotions.

By way of example, a unit administration form of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may be 0.01 to 100 mg/kg and preferentially 0.02 to 50 mg/kg, in one or more intakes.

There may be special cases in which higher or lower dosages are appropriate; such dosages are not outside the scope of the invention. According to the usual practice, the dosage that is appropriate for each patient is determined by the doctor according to the mode of administration, the weight and the response of the said patient.

According to another of its aspects, the present invention also relates to a method for treating the pathological conditions indicated above, which comprises the administration, to a patient, of an effective dose of a compound according to the invention, or a pharmaceutically acceptable salt thereof The compounds according to the invention may also be used for the preparation of compositions for veterinary use.

The invention claimed is:

1. Compound corresponding to formula (I):

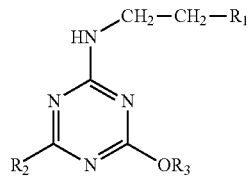

wherein:
R$_1$ is a phenyl substituted one or more substituents independently chosen from halogen, -Alk and —OAlk;
R$_2$ is:
  phenyl substituted one or more substituents independently chosen from halogen, cyano, hydroxyl, nitro, -Alk, —OAlk, —SAlk, —SO$_2$Alk, —COAlk, —SO$_2$NR$_4$R$_5$, —(C$_1$-C$_6$)alkyl-OH, —(C$_1$-C$_4$)alkyl-COOAlk, —O—(C$_1$-C$_4$)alkyl-R$_6$, methylenedioxy and an ethylenedioxy; or
  heteroaromatic unsubstituted or substituted one or more substituents independently chosen from halogen, cyano, -Alk, —OAlk, —SAlk or —N(Alk)$_2$;
R$_3$ is Alk;
R$_4$ a is hydrogen or a (C$_1$-C$_4$)alkyl;
R$_5$ a is hydrogen, (C$_3$-C$_6$)cycloalkyl or (C$_1$-C$_4$)alkyl-O-Alk;

or alternatively R$_4$ and R$_5$, together with the nitrogen atom to which they are attached, constitute a heterocyclic radical chosen from: azetidin-1-yl, pyrrolidin-1-yl, piperid-1-ylor morpholin-4-yl;
R$_6$ group is —COOAlk, —CONH$_2$ or —NHSO$_2$Alk;
wherein Alk is (C$_1$-C$_4$)alkyl, unsubstituted or substituted one or more halogen;
in the form of the base or of an acid-addition salt.

2. The compound of formula (I) according to claim 1, wherein:
R$_1$ is phenyl substituted with halogen or —OAlk;
R$_2$ is:
  phenyl substituted with one or two substituents independently chosen from halogen, cyano, hydroxyl, nitro, (C$_1$-C$_4$)alkyl, (C$_1$-C$_4$)alkoxy, —S—(C$_1$-C$_4$)alkyl, —SO$_2$—(C$_1$-C$_4$)alkyl, —CO—(C$_1$-C$_4$)alkyl, —SO$_2$NR$_4$R$_5$, (C$_1$-C$_6$)alkyl-OH, (C$_1$-C$_4$)alkyl-COO—(C$_1$-C$_4$)alkyl, —O—(C$_1$-C$_4$)alkyl-R$_6$, methylenedioxy and ethylenedioxy; or
  heteroaromatic chosen from pyridyl, indolyl, benzofuryl, benzothienyl, benzoxadiazolyl, quinolyl and isoquinolyl; wherein the heteroaromatic is unsubstituted or substituted with one or two halogen, cyano, (C$_1$-C$_4$) alkyl, (C$_1$-C$_4$)alkoxy, —S—(C$_1$-C$_4$)alkyl or an N—[(C$_1$-C$_4$) alkyl]$_2$;
R$_3$ is Alk;
R$_4$ is hydrogen;
R$_5$ is hydrogen, (C$_3$-C$_6$)cycloalkyl or (C$_1$-C$_4$)alkyl-O-Alk;
or alternatively R$_4$ and R$_5$, together with the nitrogen atom to which they are attached, constitute a morpholin-4-yl radical;
R$_6$ is —COO—(C$_1$-C$_4$)alkyl, —CONH$_2$, —NHSO$_2$—(C$_1$-C$_4$)alkyl;
wherein Alk is (C$_1$-C$_4$)alkyl, unsubstituted or substituted with one or more halogen; in the form of the base or of an acid-addition salt.

3. Compounds of formula (I) according to claim 1, in which:
R$_1$ is 4-fluorophenyl, 4-(fluoromethoxy)phenyl, 4-(difluoromethoxy)phenyl or 4-(trifluoromethoxy)phenyl;
R$_2$ is:
  3-methoxyphenyl, 3-isopropoxyphenyl, 3,4-dimethoxyphenyl, 3-nitrophenyl, 4-(methylthio)phenyl, 3-(3-methoxy-3-oxopropyl)phenyl, 3,4-methylenedioxyphenyl, 3,4-ethylenedioxyphenyl, 3-(methylsulfonyl)phenyl, 3-acetyl-2-fluorophenyl, 3-[(cyclopropylamino)sulfonyl]phenyl, 3-[(cyclopropylamino)sulfonyl]-4-methoxyphenyl, 4-chloro-3-(1-hydroxy-1-methylethyl)phenyl, 4-fluoro-3-(1-hydroxy-1-methylethyl)phenyl, 4-(1-hydroxy-1-methylethyl)-3-methoxyphenyl, 3-(1-hydroxy-1-methylethyl)phenyl, 3-(1-hydroxy-1-methylethyl)-4-methoxyphenyl, 3-[(cyclopropylamino)sulfonyl]-4-(hydroxymethyl)phenyl, 4-chloro-3-{[(2-methoxyethyl)amino]sulfonyl}phenyl, 4-chloro-3-morpholin-4-ylsulfonyl)phenyl, 3-[(cyclopropylamino)sulfonyl]-4-methylphenyl, 3-(1-ethyl-1-hydroxypropyl)phenyl, 4-chloro-3-hydroxyphenyl, 4-chloro-3-[(cyclopropylamino)sulfonyl]phenyl, 4-chloro-3-(2-ethoxy-2-oxoethoxy)phenyl, 3-cyano-4-methoxyphenyl, 3-(2-amino-2-oxoethoxy)-4-chlorophenyl, 4-chloro-3-{3-[(methylsulfonyl)amino]propoxy}phenyl; or
  6-(dimethylamino)pyridin-3-yl, 5-bromo-1H-indol-2-yl, 4-chloro-1H-indol-2-yl, 5-chloro-1H-indol-2-yl, 5-fluoro-1H-indol-2-yl, 6-fluoro-1H-indol-2-yl, 5-methyl-1H-indol-2-yl, 4-methoxy-1H-indol-2-yl, 5-methoxy-1H-indol-2-yl, 5-cyano-1H-indol-2-yl, 5-(methylthio)-1H-indol-2-yl, 1H-indol-4-yl, 1H-indol-5-yl, 1H-indol-6-yl, 1-benzofuran-2-yl, 2,1,3-benzoxadiazol-5-yl, quinolin-3-yl, quinolin-4-yl, quinolin-5-yl, quinolin-6-yl, quinolin-8-yl, 5-fluoroquinolin-8-yl, 8-methylquinolin-5-yl, 8-methoxy-2-methylquinolin-5-yl, isoquinolin-4-yl, isoquinolin-5-yl, 1-benzothien-2-yl, 5-methoxy-1-benzofuran-2-yl, or 5-chloro-1-benzofuran-2-yl; and $R_3$ is methyl or fluoromethoxy;

in the form of the base or of an acid-addition salt.

4. The compound according to claim 1 of formula (I) chosen from:

N-[2-(4-fluorophenyl)ethyl]-4-methoxy-6-(3-methoxyphenyl)-1,3,5-triazin-2-amine;
4-chloro-1H-indol-2-yl)-N-[2-(4-fluorophenyl)ethyl]-6-methoxy-1,3,5-triazin-2-amine;
4-(3,4-dimethoxyphenyl)-N-[2-(4-fluorophenyl)ethyl]-6-methoxy-1,3,5-triazin-2-amine;
4-(5-fluoro-1H-indol-2-yl)-N-[2-(4-fluorophenyl)ethyl]-6-methoxy-1,3,5-triazin-2-amine;
4-(4-chloro-1H-indol-2-yl)-N-{2-[4-(difluoromethoxy)phenyl]ethyl}-6-methoxy-1,3,5-triazin-2-amine;
4-(5-bromo-1H-indol-2-yl)-N-[2-(4-fluorophenyl)ethyl]-6-methoxy-1,3,5-triazin-2-amine;
4-(5-chloro-1H-indol-2-yl)-N-[2-(4-fluorophenyl)ethyl]-6-methoxy-1,3,5-triazin-2-amine;
2-(4-{[2-(4-fluorophenyl)ethyl]amino}-6-methoxy-1,3,5-triazin-2-yl)-1H-indole-5-carbonitrile;
N-[2-(4-fluorophenyl)ethyl]-4-methoxy-6-(5-methyl-1H-indol-2-yl)-1,3,5-triazin-2-amine;
N-[2-(4-fluorophenyl)ethyl]-4-(5-fluoroquinolin-8-yl)-6-methoxy-1,3,5-triazin-2-amine;
2-[2-chloro-5-(4-{[2-(4-fluorophenyl)ethyl]amino}-6-methoxy-1,3,5-triazin-2-yl)phenyl]propan-2-ol;
N-cyclopropyl-3-(4-{[2-(4-fluorophenyl)ethyl]amino}-6-methoxy-1,3,5-triazin-2-yl)benzenesulfonamide;
2-[4-(4-{[2-(4-fluorophenyl)ethyl]amino}-6-methoxy-1,3,5-triazin-2-yl)-2-methoxyphenyl]propan-2-ol;
2-{2-chloro-5-[4-({2-[4-(difluoromethoxy)phenyl]ethyl}amino)-6-methoxy-1,3,5-triazin-2-yl]phenyl}propan-2-ol;
2-{2-chloro-5-[4-methoxy-6-({2-[4-(trifluoromethoxy)phenyl]ethyl}amino)-1,3,5-triazin-2-yl]phenyl}propan-2-ol;
4-(1-benzothien-2-yl)-N-[2-(4-fluorophenyl)ethyl]-6-methoxy-1,3,5-triazin-2-amine;
N-[2-(4-fluorophenyl)ethyl]-4-methoxy-6-(5-methoxy-1-benzofuran-2-yl)-1,3,5-triazin-2-amine;
2-{5-[4-({2-[4-(difluoromethoxy)phenyl]ethyl}amino)-6-methoxy-1,3,5-triazin-2-yl]-2-methoxyphenyl}propan-2-ol;
4-(5-chloro-1-benzofuran-2-yl)-N-[2-(4-fluorophenyl)ethyl]-6-methoxy-1,3,5-triazin-2-amine;
2-chloro-5-(4-{[2-(4-fluorophenyl)ethyl]amino}-6-methoxy-1,3,5-triazin-2-yl)-N-(2-methoxyethyl)benzenesulfonamide;
4-[4-chloro-3-(morpholin-4-ylsulfonyl)phenyl]-N-[2-(4-fluorophenyl)ethyl]-6-methoxy-1,3,5-triazin-2-amine;
2-{2-methoxy-5-[4-methoxy-6-({2-[4-(trifluoromethoxy)phenyl]ethyl}amino)-1,3,5-triazin-2-yl]phenyl}propan-2-ol;
N-cyclopropyl-5-[4-({2-[4-(difluoromethoxy)phenyl]ethyl}amino)-6-methoxy-1,3,5-triazin-2-yl]-2-methylbenzenesulfonamide;
2-[3-(4-{[2-(4-fluorophenyl)ethyl]amino}-6-methoxy-1,3,5-triazin-2-yl)phenyl]propan-2-ol;
3-[3-(4-{[2-(4-fluorophenyl)ethyl]amino}-6-methoxy-1,3,5-triazin-2-yl)phenyl]pentan-3-ol;
2-[5-(4-{[2-(4-fluorophenyl)ethyl]amino}-6-methoxy-1,3,5-triazin-2-yl)-2-methoxyphenyl]propan-2-ol;
N-cyclopropyl-5-(4-{[2-(4-fluorophenyl)ethyl]amino}-6-methoxy-1,3,5-triazin-2-yl)-2-(hydroxymethyl)benzenesulfonamide;
N-cyclopropyl-3-[4-({2-[4-(difluoromethoxy)phenyl]ethyl}amino)-6-methoxy-1,3,5-triazin-2-yl]benzenesulfonamide;
2-chloro-5-(4-{[2-(4-fluorophenyl)ethyl]amino}-6-methoxy-1,3,5-triazin-2-yl)phenol;
2-chloro-N-cyclopropyl-5-(4-{[2-(4-fluorophenyl)ethyl]amino}-6-methoxy-1,3,5-triazin-2-yl)benzenesulfonamide;
ethyl [2-chloro-5-(4-{[2-(4-fluorophenyl)ethyl]amino}-6-methoxy-1,3,5-triazin-2-yl)phenoxy]acetate;
5-(4-{[2-(4-fluorophenyl)ethyl]amino}-6-methoxy-1,3,5-triazin-2-yl)-2-methoxybenzonitrile;
2-[2-chloro-5-(4-{[2-(4-fluorophenyl)ethyl]amino}-6-methoxy-1,3,5-triazin-2-yl)phenoxy]acetamide;
N-{3-[2-chloro-5-(4-{[2-(4-fluorophenyl)ethyl]amino}-6-methoxy-1,3,5-triazin-2-yl)phenoxy]propyl}methanesulfonamide;
N-(3-{2-chloro-5-[4-({2-[4-(difluoromethoxy)phenyl]ethyl}amino)-6-methoxy-1,3,5-triazin-2-yl]phenoxy}propyl)methanesulfonamide;
2-{2-chloro-5-[4-({2-[4-(difluoromethoxy)phenyl]ethyl}amino)-6-methoxy-1,3,5-triazin-2-yl]phenoxy}acetamide;
2-{2-chloro-5-[4-({2-[4-(fluoromethoxy)phenyl]ethyl}amino)-6-methoxy-1,3,5-triazin-2-yl]phenyl}propan-2-ol;
2-{5-[4-({2-[4-(fluoromethoxy)phenyl]ethyl}amino)-6-methoxy-1,3,5-triazin-2-yl]-2-methoxyphenyl}propan-2-ol;
2-{2-chloro-5-[4-(fluoromethoxy)-6-{[2-(4-fluorophenyl)ethyl]amino}-1,3,5-triazin-2-yl]phenyl}propan-2-ol; and
2-{5-[4-(fluoromethoxy)-6-{[2-(4-fluorophenyl)ethyl]amino}-1,3,5-triazin-2-yl]-2-methoxyphenyl}propan-2-ol;

in the form of the base or of an acid-addition salt.

5. Process for preparing the compounds of formula (I) according to claim 1, the process comprising:

reacting a compound of formula:

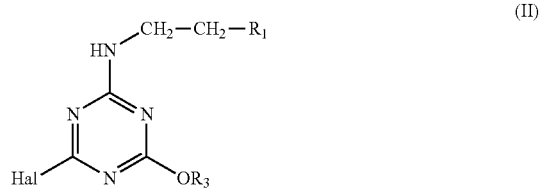

wherein $R_1$ and $R_3$ are as defined for a compound of formula (I) and, Hal is halogen, with a boronic acid or (IIIa) or an ester derivative of formula (IIIb):

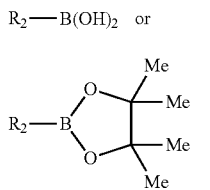

wherein R$_2$ is as defined for a compound of formula (I) in claim 1.

6. A process for preparing the compounds of formula (II)

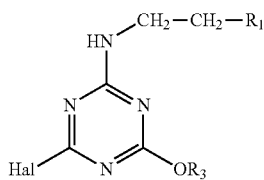

wherein
R$_1$ phenyl substituted with one or more substituents independently chosen from halogen, -Alk and —OAlk;
R$_3$ is Alk; and
Hal is halogen;

the process comprising:
reacting a compound of formula:

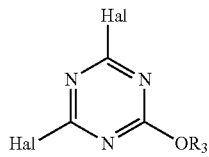

wherein
R$_3$ is -Alk and
Hal is halogen;
with a compound of formula (V):

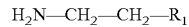

wherein
R$_1$ is phenyl substituted with one or more substituents independently chosen from halogen, -Alk and —OAlk.

7. A pharmaceutical composition, comprises a compound of formula (I) according to claim 1, or a pharmaceutically acceptable salt thereof, and at least one pharmaceutically acceptable excipient.

\* \* \* \* \*